(12) United States Patent
Kawabe et al.

(10) Patent No.: US 7,407,985 B2
(45) Date of Patent: Aug. 5, 2008

(54) COMPOUNDS THAT ABROGATE DNA DAMAGE INDUCED CELL CYCLE G2 CHECKPOINT AND/OR AUGMENT ANTI-CANCER ACTIVITY OF DNA-DAMAGING TREATMENTS

(75) Inventors: Takumi Kawabe, Numazu (JP); Hidetaka Kobayashi, Numazu (JP)

(73) Assignee: Canbas Co., Ltd., Numazu, Shizuoka (JP)

( * ) Notice: Subject to any disclaimer, the term of this patent is extended or adjusted under 35 U.S.C. 154(b) by 280 days.

(21) Appl. No.: 11/334,160

(22) Filed: Jan. 17, 2006

(65) Prior Publication Data
US 2006/0122269 A1 Jun. 8, 2006

Related U.S. Application Data

(62) Division of application No. 10/457,029, filed on Jun. 6, 2003, now Pat. No. 7,030,111.

(60) Provisional application No. 60/386,930, filed on Jun. 6, 2002.

(51) Int. Cl.
| | |
|---|---|
| A61K 31/21 | (2006.01) |
| A61K 31/235 | (2006.01) |
| A61K 31/495 | (2006.01) |
| A61K 31/497 | (2006.01) |
| A61K 31/535 | (2006.01) |
| A61K 31/5375 | (2006.01) |

(52) U.S. Cl. ........................ 514/510; 514/513; 514/538; 514/540; 514/544; 514/532; 514/231.2; 514/237.5; 514/252.1; 514/252.12

(58) Field of Classification Search ................ 544/106, 544/170, 171, 224, 336, 358; 546/302; 514/231.2, 514/237.5, 252.1, 252.12, 532, 510, 513, 514/538, 540, 544
See application file for complete search history.

(56) References Cited

U.S. PATENT DOCUMENTS

| 4,394,389 A | 7/1983 | Van't Riet et al. |
| 5,200,550 A | 4/1993 | Shroot et al. .................. 560/64 |
| 6,211,164 B1 | 4/2001 | Luo et al. |
| 6,881,575 B1 | 4/2005 | Suganuma et al. |
| 7,202,244 B2 * | 4/2007 | Boyle et al. .................. 514/247 |
| 2004/0248783 A1 | 12/2004 | Kawabe et al. |

FOREIGN PATENT DOCUMENTS

| CN | 1226826 A | 8/1999 |
| DE | 20 49 865 | 4/1972 |
| EP | 0 409 728 | 1/1991 |
| WO | 97/46228 | 12/1997 |
| WO | 99/15157 | 4/1999 |
| WO | 99/47522 | 9/1999 |
| WO | 99/48495 | 9/1999 |
| WO | 01/21771 | 3/2001 |

OTHER PUBLICATIONS

Chemical Abstracts, vol. 58, No. 6, Mar. 18, 1963, Columbus, Ohio, US; abstract No. 5563c, K.C. Joshi et al.: "Synthesis of fluorobenzoates as possible pesticides.", p. 5563; col. 1; XP002266801, abstract & J. Indian Chem. Soc., vol. 39, No. 7, 1962, pp. 495-496.

Chemical Abstracts, vol. 58, No. 4, Feb. 18, 1963, Columbus, Ohio, US; abstract No. 3341g, S.D. Jolad et al.: "Substituted benzophenones.", p. 3341; col. 1; XP002266802, abstract & J. Karnatak Univ., vol. 5, 1960, pp. 1-9.

Database Crossfire Beilstein 'Online! Beilstesin Institut Zur Foederung Der Chemischen Wissenschaften, Frankfurt AM Main, DE; Database-Accession No. 2274611 (BRN), XP002266804 & J. Org. Chem., vol. 41, 1976, p. 2443.

Database Crossfire Beilstein 'Online! Beilstesin Institut Zur Foederung Der Chemischen Wissenschaften, Frankfurt AM Main, DE; Database-Accession No. 2583565 (BRN), XP002266805 & Arch. Pharm. Dtsch. Pharm. Ges., vol. 296, 1963, p. 522-527.

Database Crossfire Beilstein 'Online! Beilstesin Institut Zur Foederung Der Chemischen Wissenschaften, Frankfurt AM Main, DE; Database-Accession No. 6608813 (BRN), XP002266806 & J. Org. Chem. USSR (Engl. Transl.), vol. 28, No. 8.2, 1992, pp. 1339-1344.

Database Crossfire Beilstein 'Online! Beilstesin Institut Zur Foederung Der Chemischen Wissenschaften, Frankfurt AM Main, DE; Database-Accession No. 2649250, 2585603 (BRN), XP002266807 & Anal. Chem., vol. 56, No. 12, 1984, pp. 2038-2043.

Database Crossfire Beilstein 'Online! Beilstesin Institut Zur Foederung Der Chemischen Wissenschaften, Frankfurt AM Main, DE; Database-Accession No. 2120541 (BRN), XP002266808 & J. Prakt. Chem., vol. 321, 1979, p. 969,973.

Database Crossfire Beilstein 'Online! Beilstesin Institut Zur Foederung Der Chemischen Wissenschaften, Frankfurt AM Main, DE; Database-Accession No. 3295520 (BRN), XP002266809 & J. Org. Chem., vol. 21, 1956, p. 671.

(Continued)

*Primary Examiner*—Cecilia Tsang
*Assistant Examiner*—Kristin Bianchi
(74) *Attorney, Agent, or Firm*—Pillsbury Winthrop Shaw Pittman LLP

(57) ABSTRACT

The invention provides compositions and methods to inhibit the cell cycle G2 checkpoint, in particular the DNA-damage-induced G2 checkpoint, in mammalian cells including human cells. Specifically, the invention provides compositions and methods to sensitize cells to DNA-damaging agents by abrogating the cell cycle G2 checkpoint. Compounds of the invention are used to treat proliferative disorders such as cancer. The invention provides compositions and methods for selectively sensitizing G1 checkpoint impaired cancer cells to DNA-damaging agents and treatments.

27 Claims, 12 Drawing Sheets

OTHER PUBLICATIONS

Database Crossfire Beilstein 'Online! Beilstesin Institut Zur Foederung Der Chemischen Wissenschaften, Frankfurt AM Main, DE; Database-Accession No. 2121991 (BRN), XP002266810 & Tetrahedron., vol. 47, No. 4/5, 1991, pp. 767-776, Oxford GB.

Chemical Abstracts, vol. 92, No. 22, Jun. 2, 1980, Columbus, Ohio, US; abstract No. 189424a, Deutscher H.J. et al.: "Liquid-crystalline hydroquinone bis(trans-4-n-alkylcyclohexanecarboxylates).", p. 559; col. 2; XP002266803, abstract & J. Prakt. Chem., vol. 321, No. 6, 1979, pp. 969-977.

Zoe A. Stewart and Jennifer A. Pientenpol: "G2 Checkpoint and Anticancer Therapy", Eureka, 'Online!, Jan. 25, 2001, pp. 1-28, XP002280757, Retrieved from the Internet: <URL:http://www.eurekah.com/pietenpol/> retrieved on May 18, 2004!, p. 11-p. 14.

Antonio M. Serafin et al.: "Chemosensitivity of prostatic tumour cell lines under conditions of G2 block abrogation", UROL Res, vol. 29, 2001, pp. 221-227, XP002280758, abstract; p. 227, reference 2.

Piers Edward et al.: "Improved Synthesis of Isogranualtimide, a G2 Checkpoint Inhibitor. Syntheses of Didemnimide C, Isodidemnimide A, Neodidemnimide A, 17-Methylgranulatimide, and Isogranulatimides A-C", Journal of Organic Chemistry, American Chemical Society. Easton, US, vol. 65, Jan. 28, 2000, pp. 530-535, XP002175370, ISSN: 0022-3263, p. 530, col. 2.

Yuli Wang et al.: "Radiosensitization of p53 Mutant cells by PD0166285, a novel G2 checkpoint abrogator", Cancer Research., vol. 61, Nov. 15, 2001, pp. 8211-8217, XP002280759, American Association for Cancer Research, Baltimore, MD., US, ISSN: 0008-5472, p. 8211-p. 8212.

Hartwell, "Defects in a Cell Cycle Checkpoint May Be Responsible for the Genomic Instability of Cancer Cells," *Cell*, (Nov. 13, 1992), vol. 71, pp. 543-546.

Levine, "p53, the Cellular Gatekeeper for Growth and Devision," Cell, (Feb. 7, 1997), vol. 88, pp. 323-331.

Maller, "Mitotic Control," Current Opinion in Cell Biology, (1991), vol. 3, pp. 269-275.

O'Connor, et al., "DNA damage checkpoints: Implications for cancer therapy," Progress in Cell Cycle Research, (1996), vol. 2, pp. 165-173.

Chemical Abstracts, vol. 92, No. 22, Jun. 2, 1980, Columbus, Ohio, US; abstract No. 189424e, Deutscher H.J. et al.: "Liquid-crystalline hydroquinone bis(trans-4-n-alkylcyclohexanecarboxylates).", p. 559; col. 2; XP002266803, abstract & J. Prakt. Chem., vol. 321, No. 6, 1979, pp. 969-977.

Zoe A. Stewart and Jennifer A. Pientenpol: "G2 Checkpoint and Anticancer Therapy", Eureka, 'Online!, Jan. 25, 2001, pp. 1-28, XP002280757, Retrieved from the Internet: <URL:http://www.eurekah.com/pietenpol/> retrieved on May 18, 2004!, p. 11-p. 14.

Antonio M. Serafin et al.: "Chemosensitivity of prostatic tumour cell lines under conditions of G2 block abrogation", UROL Res, vol. 29, 2001, pp. 221-227, XP002280758, abstract; p. 227, reference 2.

Piers Edward et al.: "Improved Synthesis of Isogranualtimide, a G2 Checkpoint Inhibitor. Syntheses of Didemnimide C, Isodidemnimide A, Neodidemnimide A, 17-Methylgranulatimide, and Isogranulatimides A-C", Journal of Organic Chemistry, American Chemical Society. Easton, US, vol. 65, Jan. 28, 2000, pp. 530-535, XP002175370, ISSN: 0022-3263, p. 530, col. 2.

Yuli Wang et al.: "Radiosensitization of p53 Mutant cells by PD0166285, a novel G2 checkpoint abrogator", Cancer Research., vol. 61, Nov. 15, 2001, pp. 8211-8217, XP002280759, American Association for Cancer Research, Baltimore, MD., US, ISSN: 0008-5472, p. 8211-p. 8212.

Hartwell, "Defects in a Cell Cycle Checkpoint May Be Responsible for the Genomic Instability of Cancer Cells," *Cell*, (Nov. 13, 1992), vol. 71, pp. 543-546.

Levine, "p53, the Cellular Gatekeeper for Growth and Devision," *Cell*, (Feb. 7, 1997), vol. 88, pp. 323-331.

Maller, "Mitotic Control," *Current Opinion in Cell Biology*, (1991), vol. 3, pp. 269-275.

O'Connor, et al., "DNA damage checkpoints: Implications for cancer therapy," *Progress in Cell Cycle Research*, (1996), vol. 2, pp. 165-173.

* cited by examiner

A. G2 Checkpoint abrogation by various CBDC compounds

B. Structure and G2 checkpoint abrogating activity relationship

CBDC004

4-chloro-benzoic acid 4-methoxy-phenyl ester

CBDC401

4-chloro-benzoic acid p-tolyl ester

CBDC402

4-bromo-benzoic acid p-tolyl ester

CBDC403

3, 4, 5-trifluoro-benzoic acid p-tolyl ester

CBDC404

4-fluoro-benzoic acid 4-bromo-phenyl ester

CBDC405

3, 4-dichloro-benzoic acid p-tolyl ester

CBDC406

2, 4-dichloro-benzoic acid p-tolyl ester

CBDC407

4-fluoro-benzoic acid p-tolyl ester

CBDC408
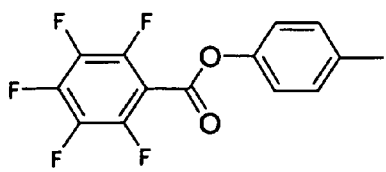
2, 3, 4, 5, 6-pentafluoro-benzoic acid p-tolyl ester
CBDC409
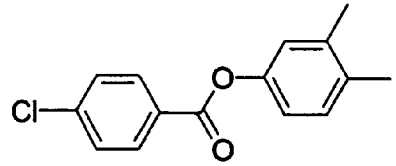
4-chloro-benzoic acid 3, 4-dimethyl-phenyl ester
CBDC410
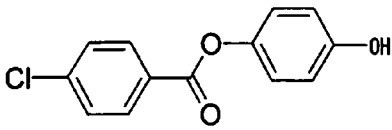
4-chloro-benzoic acid 4-hydroxy-phenyl ester
CBDC411
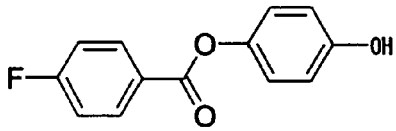
4-fluoro-benzoic acid 4-hydroxy-phenyl ester
CBDC412
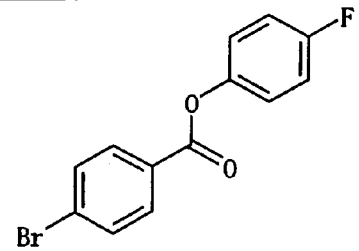
4- Bromo-benzoic acid 4-fluoro-phenyl ester
CBDC413
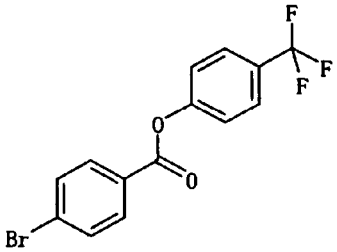
4-Bromo-benzoic acid 4-trifluoromethyl-phenyl ester
FIGURE 4, Continued

CBDC414
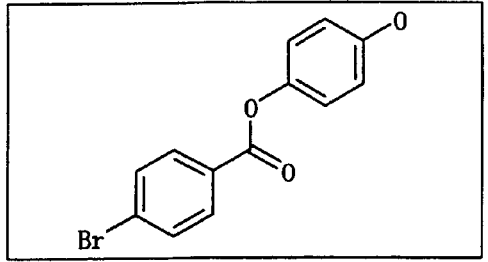
4-bromo-benzoic acid 4-hydroxy-phenyl ester
CDBC415
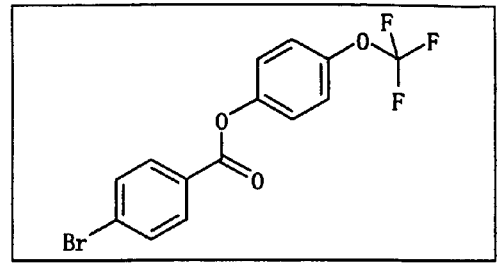
4-bromo-benzoic acid 4-trifluoromethoxy-phenyl ester
CBDC418
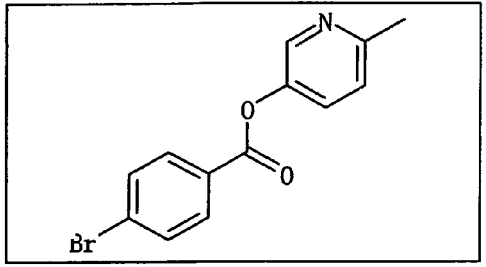
4-bromo-benzoic acid 6-methyl-pyridin-3-yl ester
CDBC440
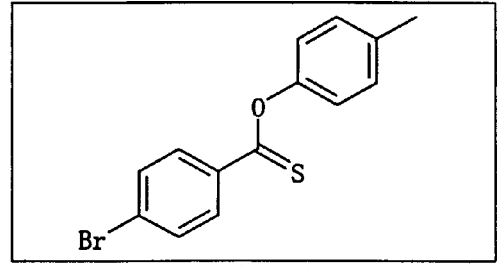
4-bromo-thiobenzoic acid O-p-tolyl ester
CBDC441
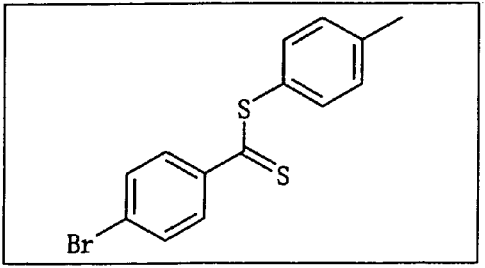
4-bromo-dithiobenzoic acid p-tolyl ester
CDBC442
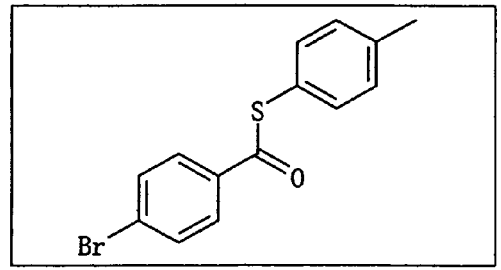
4-bromo-thiobenzoic acid S-p-tolyl ester
FIGURE 4, Continued

COMPOUNDS THAT ABROGATE DNA DAMAGE INDUCED CELL CYCLE G2 CHECKPOINT AND/OR AUGMENT ANTI-CANCER ACTIVITY OF DNA-DAMAGING TREATMENTS

RELATED APPLICATIONS

This application is a divisional of U.S. application Ser. No. 10/457,029, filed Jun. 6, 2003, now U.S. Pat. No. 7,030,111, issued Apr. 18, 2006, which claims priority to U.S. application Ser. No. 60/386,930, filed Jun. 6, 2002.

FIELD OF THE INVENTION

The present invention relates to chemical compounds having anti-cell proliferative activity, and to their production, as well as to pharmaceutical compositions containing them, and to methods of treating proliferative disorders using these compounds and compositions. The invention compounds are therefore useful for inhibiting cell proliferation and, as such, for treating cell proliferative disorders including cancer. In particular, the invention relates to compounds that abrogate the cell cycle G2 checkpoint, including the DNA-damage-induced G2 checkpoint, which are useful in treating proliferative disorders such as cancer, including treating metastatic and non-metastatic solid or liquid tumors.

BACKGROUND

The cell cycle comprises S phase (DNA replication), M phase (mitosis), and two gap phases (G1 and G2 phases) between S and M phases. Checkpoints in the cell cycle ensure accurate progression through cell cycle stages, and include monitoring the state of DNA integrity, DNA replication, cell size, and the surrounding environment (Maller (1991) *Curr. Opin. Cell Biol.*, 3:26). It is especially important for multi-cellular organisms to maintain integrity of genome, and there are multiple checkpoints that monitor the state of genome. Among them are G1 and G2 checkpoints prior to DNA replication and mitosis, respectively. It is crucial to repair or correct DNA damage before entering S phase, because once damaged DNA is replicated it often gives rise to mutations (Hartwell (1992) *Cell*, 71: 543). Progression through G1 and G2 checkpoints without repairing extensive DNA damage induces mitotic catastrophe and/or apoptosis.

Most cancer cells carry abnormalities in G1 checkpoint-related proteins such as p53, Rb, MDM-2, p16$^{INK4}$ and p19$^{ARF}$(Levine (1997) *Cell*, 88:323). Alternatively, mutations can cause overexpression and/or over-activation of oncogene products, e.g., Ras, MDM-2 and cyclin D, which reduce the stringency of G1 checkpoint. In addition to these mutations, excessive growth factor signaling can be caused by the overexpression of growth factors and can reduce the stringency of G1 checkpoint. Together with loss-of-function and gain-of-function mutations, continuous activation by growth factor receptors or downstream signal-transducing molecules can cause cell transformation by overriding the G1 checkpoint. A disrupted or abrogated G1 checkpoint contributes to higher mutation rates and the many mutations observed in cancer cells. As a result, most cancer cells depend on G2 checkpoint for survival against excessive DNA damage (O'Connor and Fan (1996) *Prog. Cell Cycle Res.*, 2:165).

The G2 cell cycle checkpoint restricts the onset of mitosis until DNA replication and repair are complete. Malfunction of the G2 checkpoint would allow premature onset of mitosis prior to the completion of DNA replication and repair, producing daughter cells lacking a substantial portion of the genomic DNA or harboring mutations. Functions of the G2 checkpoint includes detecting DNA damage and generation of signal that can lead to cell cycle arrest when DNA damage is detected. The mechanism that promotes the cell cycle G2 arrest after DNA damage is believed to be conserved among species from yeast to human. In the presence of damaged DNA, Cdc2/Cyclin B kinase is kept inactive by phosphorylation of threonine-14 and tyrosine-15 residues on Cdc2 kinase; alternately, the level of Cyclin B protein may be reduced. At the onset of mitosis, Cdc25 phosphatase removes inhibitory phosphates from Cdc2/Cyclin B kinase, thereby activating Cdc2/Cyclin B kinase. The activation of Cdc2/Cyclin B kinase is equivalent to the onset of M phase.

In fission yeast, the protein kinase Chk1 is required for the cell cycle arrest in response to damaged DNA. Chk1 kinase acts downstream of several rad gene products and is modified by the phosphorylation upon DNA damage. The kinases Rad53 of budding yeast and Cds1 of fission yeast are known to conduct signals from unreplicated DNA. It appears that there is some redundancy between Chk1 and Cds1 because elimination of both Chk1 and Cds1 culminated in disruption of the G2 arrest induced by damaged DNA. Interestingly, both Chk1 and Cds1 phosphorylate Cdc25 and promote Rad24 binding to Cdc25, which sequesters Cdc25 to cytosol and prevents Cdc2/Cyclin B activation. Therefore Cdc25 appears to be a common target of these kinases implying that this molecule is an indispensable factor in the G2 checkpoint.

In humans, both hchk1, a human homologue of fission yeast Chk1, and Chk2/HuCds1, a human homologue of the budding yeast Rad53 and fission yeast Cds1, phosphorylate Cdc25C at serine-216, a critical regulatory site, in response to DNA damage. This phosphorylation creates a binding site for small acidic proteins 14-3-3s, human homologues of Rad24 and Rad25 of fission yeast. The regulatory role of this phosphorylation was clearly indicated by the fact that substitution of serine-216 to alanine on Cdc25C disrupted cell cycle G2 arrest in human cells. However, the mechanism of G2 checkpoint is not fully understood.

SUMMARY

This invention provides compounds that can be used to treat cell proliferation disorders, such as those associated with benign and malignant cancer cells and further provides pharmaceutical compositions containing them. While the invention is not limited to any particular mechanism, it is believed that compounds of the invention can function by inhibiting, disrupting, or abrogating the G2 checkpoint, in particular by abrogating the DNA-damage-induced G2 checkpoint. Compounds of the invention can act as anti-cancer agents by selectively sensitizing cells with DNA damage, e.g., cancer cells, to the effects of DNA damage. Compounds of the invention can sensitize cells, in particular cancer cells, to the effects of DNA-damaging agents or treatments. Compounds of the invention can suppress cell growth without any additional DNA-damaging treatment, and little or no cytotoxic activity against normal cells. Thus, compounds of invention can be used as anti-cancer agents, and as active ingredients in pharmaceutical compositions used as anti-cancer medicines, with or without any additional DNA-damaging treatment.

The invention provides methods for treating cells having proliferative disorders. The invention provides a method for abrogating the G2 checkpoint of a cell, in particular a method for abrogating the DNA-damage-induced G2 checkpoint, by contacting the cell with a compound of the invention or a pharmaceutical composition of the invention in an amount sufficient to abrogate the G2 checkpoint. The invention further provides a method for selectively sensitizing a cell with an impaired G1 checkpoint to a DNA-damaging agent comprising, contacting the cell with a compound of the invention or a pharmaceutical composition of the invention in an amount sufficient to abrogate the G2 checkpoint, thereby sensitizing the cell to the DNA-damaging agent. The cell can be a mammalian cell, in particular a human cell, more particularly a human cancer cell.

The invention provides a method for inducing mitotic catastrophe and/or apoptosis in a cell in an individual by administering a compound of the invention or a pharmaceutical composition of the invention, in an amount sufficient to abrogate the G2 checkpoint in the cell and thereby sensitizing the cell to a DNA-damaging agent, and administering a DNA-damaging agent. The cell can be a mammalian cell, in particular a human cell, in particular a human cancer cell. The cancer cell can have an impaired G1 cell cycle arrest checkpoint. The DNA-damaging agent can be 5-fluorouracil (5-FU), rebeccamycin, adriamycin, bleomycin, cisplatin, hyperthermia, UV irradiation or gamma-irradiation, or any suitable compounds that are known to cause DNA damage and/or are identified by a screening method, e.g., as described in U.S. patent application Ser. No. 09/667,365.

BRIEF DESCRIPTION OF THE DRAWINGS

FIG. 3a shows a dose-response curve for G2 checkpoint abrogation by various CBDC compounds and FIG. 3b illustrates structure-activity relationships of CBDC compounds.

FIG. 10a shows that CBDC402 abolishes the bleomycin-induced increase of activated normal T cells in G2 phase; FIG. 10b shows that CBDC402 abolishes the large bleomycin-induced increase of leukemic T cells (Jurkat cells) in G2 phase; FIG. 10c shows that CBDC402 does not affect the colchicine-induced increase of activated normal T cells in M phase.

DETAILED DESCRIPTION OF THE INVENTION

Figure 1:
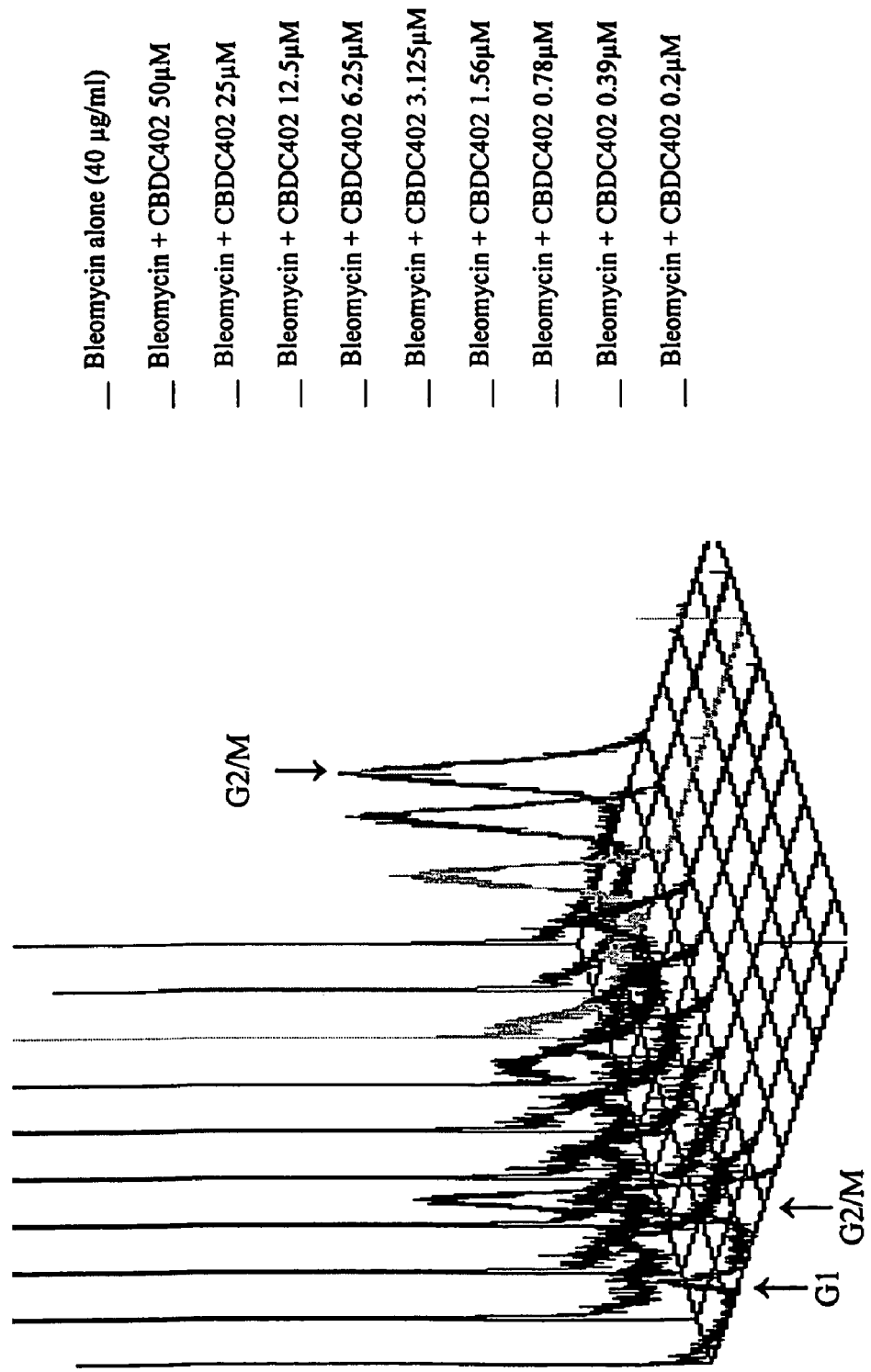
FIG. 1 shows the results of flow cytometry analysis of the DNA content of Jurkat cells after the treatment with bleomycin (40 ug/ml), or bleomycin plus CBDC402 at various concentrations (0.2, 0.39, 0.78, 1.56, 3.125, 6.25, 12.5, 25 and 50 ug/ml) for 24 hrs.

The invention provides compositions and methods for treating cell proliferation disorders. Specifically, the invention provides compounds that abrogate the cell cycle G2 checkpoint, which can be used to treat cell proliferation disorders such as those associated with cancer. The invention provides pharmaceutical compositions that contain one or more compounds of the invention in a suitable carrier or excipient, wherein these compositions may include additional active ingredients such as DNA-damaging agents. The invention provides methods for using compounds of the invention, and pharmaceutical compositions containing compounds of the invention, to suppress or kill proliferating cells, in particular cells with proliferation disorders. The invention further provides methods for using compounds of the invention to selectively sensitize a cell to the effects of other agents or treatments including DNA-damaging agents.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "abrogate the cell cycle G2 checkpoint" or "inhibit the cell cycle G2 checkpoint" or "disrupt the cell cycle G2 checkpoint" or "abrogation of the G2 checkpoint" any grammatical equivalent of the term, refers to the ability of compounds of the invention to abrogate the ability of a cell to arrest the cell cycle at the G2 checkpoint. Abrogation of cell cycle G2 checkpoint includes abrogation under conditions in the cell that otherwise would cause G2 cell cycle arrest, such as the accumulation of DNA damage by, e.g., certain antitumor agents, X-ray irradiation, gamma-ray irradiation, UV irradiation, or hyperthermia. Abrogation of the G2 checkpoint under such conditions is considered "abrogation of the G2 checkpoint" but more particularly, abrogation of "the DNA-damage-induced G2 checkpoint," where it is understood that the DNA-damage-induced G2 checkpoint includes recognition of DNA damage and generation of a signal that normally produces G2 cell cycle-arrest. A cell in which the cell cycle G2 checkpoint is abrogated exhibits a decrease in the length of time that the cell is in the G2 checkpoint, which can range from absence of G2 checkpoint altogether (G2 checkpoint arrest) to a G2 checkpoint having a decrease in duration of minutes, hours, days, weeks or longer under appropriate conditions. Thus, a cell contacted with a compound of the invention has a G2 checkpoint time shorter in length than the cell normally would have in the absence of the compound. For example, a decrease in the length of G2 checkpoint time would mean that a cell which is in G2 for a certain time, e.g., 4 hours, when contacted with an invention compound, is in G2 for less than 4 hours, e.g., 3.5, 3, 2.5, 2, 1 or fewer hours. The term "G2 abrogation" or "G2 checkpoint abrogation" or "G2 checkpoint inhibitory activity" or any grammatical equivalent, means any amount of abrogation or inhibition of the G2 checkpoint.

As used herein, the term "apoptosis" refers to programmed cell death, and associated changes in cell physiology, including nucleic acid fragmentation, caspase activation, chromosome condensation, etc., as is understood in the art. The term "mitotic catastrophe" means cell death resulting from an error in the mitotic process.

As used herein, the terms "DNA-damaging treatment" and "DNA-damaging agent" mean any treatment regimen that directly or indirectly damages DNA. Specific examples of DNA-damaging agents include alkylating agents, nitrosoureas, anti-metabolites, plant alkaloids, plant extracts and radioisotopes. Specific examples of agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubibcin (Cerubicine), idarubicin (Idamycin) and epirubicin (Ellence), anthracyclin analogues such as mitoxantrone, actinimycin D, non intercalating topoisomerase inhibitors such as epipodophyllotoxins (etoposide=VP16, teniposide=VM-26), podophylotoxin, bleomycin (Bleo), pepleomycin, compounds that form adducts with nucleic acid including platinum derivatives, e.g., cisplatin (CDDP), trans analogue of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or α-, β-, or γ-radiation, as well as environmental shock, e.g., hyperthermia. One of skill in the art can identify and use other DNA-damaging agents and treatments.

The term "compound of the invention" is intended to mean a molecule that has the structure and activity disclosed herein. A compound of the invention can be isolated, pure, substantially pure, or may be in a composition containing a mixture of other components. Purity of a composition containing a compound of the invention can be determined, for example, using analytical chemistry techniques such as high performance liquid chromatography (HPLC). A composition as provided herein may contain one or more compounds of the invention, in a mixture with suitable carriers, excipients, additional active ingredients including DNA-damaging agents, and the like.

The term "pharmaceutical composition" refers to a composition suitable for pharmaceutical use, e.g., as a anti-cancer agent, in a subject. The subject may be a human in need of treatment for a cell proliferation disorder. A pharmaceutical composition of the invention is a formulation that comprises a pharmacologically effective amount of at least one compound of the invention and a pharmaceutically acceptable carrier.

As used herein, the terms "proliferative disorder" and "proliferative condition" mean any pathological or non-pathological physiological condition characterized by aberrant or undesirable proliferation of at least one cell, including conditions characterized by undesirable or unwanted cell proliferation or cell survival conditions characterized by deficient or aberrant or deficient apoptosis, as well as conditions characterized by aberrant or undesirable or unwanted cell survival. The term "differentiative disorder" means any pathological or non-pathological physiological condition characterized by aberrant or deficient differentiation.

The term "subject" refers to animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., tumor bearing mice).

As used herein, the singular forms "a", "and," "the" and "is" include plural referents unless the context clearly indicates otherwise. Thus, for example, reference to a "compound" includes a plurality of compounds and reference to "a residue" or an "amino acid" includes reference to one or more residues and amino acids.

All publications, patents, and patent applications cited herein are hereby expressly incorporated by reference for all purposes.

G2 Checkpoint Abrogation

While the invention is not limited to a particular mechanism of action, it has been observed that compounds of the invention can abrogate the G2 checkpoint in proliferating cells. The G2 cell cycle checkpoint restricts the onset of mitosis until DNA replication and repair are complete, and disruption of the G2 checkpoint would allow premature onset of mitosis prior to the completion of DNA replication and repair. Without wishing to be limited to this theory, it is believed that, in cells that have accumulated DNA damage, abrogation of the G2 checkpoint by compounds of the invention means the cells do not have an opportunity to correct or repair DNA damage at the G2 checkpoint and instead, proceed through G2 without DNA repair, which leads to mitotic catastrophe, apoptosis, or other conditions resulting in cell suppression or cell death.

In accordance with one aspect, the invention provides methods for abrogating the G2 cell cycle arrest induced by DNA damage. There are significant differences cell cycle responses, in particular in the G2 checkpoint, in normal cells and in DNA-damaged cells. The damage-induced G2 checkpoint includes recognition of DNA damage and generation of a signal that produces cell cycle-arrest. The invention provides compounds that selectively abrogate the DNA-damage-induced G2 checkpoint.

In accordance with another aspect, the invention provides compounds and pharmaceutical compositions that sensitize cells to DNA-damaging agents and treatments. The invention provides methods for sensitizing cells to DNA-damaging agents and treatments.

In accordance with another aspect, the invention provides compounds and pharmaceutical compositions that selectively target cells with DNA damage. The invention further provides methods for selectively targeting cells with DNA damage by contacting the cells with at least one compound of the invention in an amount sufficient to abrogate DNA-damage-induced G2 checkpoint. In one embodiment, cells with pre-existing DNA damage are treated with compounds of the invention that abrogate the G2 checkpoint, and the DNA-damaged cells proceed through G2 phase, which results in cell death or suppression (usually, mitotic catastrophe or apoptosis). In another embodiment, cells are treated a combination of at least one DNA-damaging agent and at least one compound of the invention, resulting in a higher rate of cell death or suppression than the rate seen using DNA-damaging agents alone.

In accordance with another aspect, the present invention provides compounds and pharmaceutical compositions that selectively target cells with an impaired G1 cell cycle checkpoint, in particular cancer cells. The invention provides methods for selectively targeting cells with an impaired G1 cell cycle checkpoint, in particular cancer cells, by contacting the cells with at least one compound of the invention in an amount sufficient to abrogate G2 cell cycle checkpoint. Without wishing to be limited by this theory, cells with an impaired G1 cell cycle checkpoint do not repair DNA damage prior to G1, and abrogation of the G2 checkpoint by compounds of the present invention means these cells proceed through mitosis without repairing accumulated DNA damage. The lack of an effective G2 checkpoint after DNA damage becomes fatal to the cell having G1 checkpoint defect. If a cell progresses through G2 without sufficient repair of DNA damage, the damage can lead to mitotic catastrophe or apoptosis.

In accordance with one aspect, the present invention provides compounds that selectively target cancer cells, and kill or suppress growth of cancer cells. The invention further provides methods for selectively targeting cancer cells, and killing or suppressing growth of cancer cells, by contacting the cells with at least one compound of the invention in an amount sufficient to abrogate the G2 checkpoint. Many cancer cells have mutations in genes involved in the G1 cell cycle arrest checkpoint, including impaired tumor suppressor genes such as p53, Rb, p16INK4, and p19ARF, and/or mutations that cause expression of oncogenes such as MDM-2 and cyclin D. In addition, overriding the G1 checkpoint can lead to transformation of normal cells into cancer cells, as excessive growth factor signaling caused by the overexpression of growth factors, can lead to a condition wherein growth factor receptors or downstream signal-transducing molecules cause cell transformation by overriding the G1 checkpoint. In contrast, few cancers have disrupted G2 cell cycle arrest checkpoints. Thus, the G2 checkpoint is usually retained in cancer cells with an impaired G1 checkpoint. Selective disruption of the G2 checkpoint would make cancer cells with an impaired G1 checkpoint more sensitive to DNA-damaging treatment, as compared to normal cells with an intact G1 checkpoint, since progression through G1 and G2 without repairing such damage induces apoptosis or mitotic catastrophe. Without wishing to be limited to this theory, compounds of the present invention selectively disrupt (abrogate) the G2 checkpoint in cancer cells, thereby causing cancer cells with an impaired G1 checkpoint to be more sensitive to DNA-damaging treatment. Accordingly, the invention provides compounds that sensitize G1-checkpoint-impaired cancer cells to DNA-damaging agents and treatments.

In accordance with another aspect of the invention, compounds of the invention can selectively target cancer cells with little or no cytotoxic effect on normal cells. Without wishing to be limited by this theory, it is proposed that a normal cell in which the G2 checkpoint is abrogated by a compound of the invention will suffer little or no deleterious consequences from entering G2 phase and undergoing mitosis without a functioning G2 checkpoint; in contrast, abrogation of the DNA-damaged G2 checkpoint in a DNA-damaged cell by a compound of the invention is expected to have severe cytotoxic effects, leading to apoptosis or mitotic catastrophe. Thus, the invention provides methods for selectively targeting DNA-damaged cells such as cancer cells, with little or no cytotoxic effect on normal (undamaged) cells, by contacting the cells with at least one compound of the invention in an amount sufficient to abrogate the G2 checkpoint. The provides pharmaceutical compositions containing at least one compound of the invention, suitable for use in methods for selectively targeting targeting DNA-damaged cells such as cancer cells, with little or no cytotoxic effect on normal (undamaged) cells.

In accordance with yet another aspect of the invention, compounds of the invention can selectively sensitize cells, in particular cancer cells, to the cell killing effects of DNA-damaging agents with little or no cytotoxic effect on normal cells. Most conventional anti-cancer agents target proliferating cells irrespective of whether they are cancer cells or normal cells, with the result that most conventional anti-cancer medicines give rise to side effects such as nausea, diarrhea, or hair loss. In contrast, compounds of the present invention selectively target cells with impaired G1 checkpoint, or other types of DNA damage, and therefore have little or no cytotoxic effect on normal cells.

The invention provides a method for inducing apoptosis or mitotic catastrophe in a cell by contacting the cell with at least one compound of the invention in an amount sufficient to abrogate the G2 checkpoint. The invention further provides a method for inducing apoptosis or mitotic catastrophe in a cell by contacting the cell with at least one pharmaceutical composition of the invention in an amount sufficient to abrogate the G2 checkpoint. The cell can be a cell with DNA damage, in particular a cancer cell.

The invention provides a method for inducing apoptosis or mitotic catastrophe in a cell by contacting the cell with a DNA-damaging agent or treatment and at least one compound of the invention in an amount sufficient to abrogate the G2 checkpoint and thereby sensitize the cell to the DNA-damaging agent or treatment. The cell can be a cancer cell. The cancer cell can have an impaired G1 cell cycle checkpoint. The DNA-damaging agent or treatment can be 5-flourouracil (5-FU), rebeccamycin, adriamycin, bleomcin, cisplatin, hyperthermia, UV irradiation, gamma-irradiation, or other DNA-damaging agent or treatment sufficient to cause damage.

In accordance with one aspect, the invention provides a method for screening for compounds capable of abrogating the G2 checkpoint by: (a) providing a test compound; (b) providing a population of cells; (c) administering to the population of cells an agent that causes accumulation of G2/M phase cells after treatment; (d) administering the test compound to a portion of the population treated with the agent that causes accumulation of G2/M phase cells; (e) measuring the number of cells in G2/M phase in the population treated with the test compound; (f) measuring the number of cells in G2/M phase in the population treated only with the agent that causes accumulation of G2/M phase cells; (g) comparing the number in (e) with the number in (f) to determine whether the test compound abrogated the G2 cell cycle checkpoint. According to this method, accumulation of cells in G2/M phase is used as an indicator of G2 cell cycle arrest. In one embodiment, the agent induces DNA damage, and the method is useful for screening for compounds capable of abrogating the DNA-damage-induced G2 checkpoint. In another embodiment, the amount of DNA is measured using flow cytometry, e.g., using propidium iodine to stain DNA and FACS™ analysis, or the equivalent, to determine cell cycle stage by measuring the DNA content of each cell. In one embodiment, the amount of DNA is measured after about 10 to about 72 hours after the contacting step.

The invention provides compounds that, when administered to a cell, abrogate the G2 checkpoint, in particular the DNA-damage-induced G2 checkpoint, and kill or suppress cells, with or without DNA-damaging treatment, wherein the compounds have the following general structure:

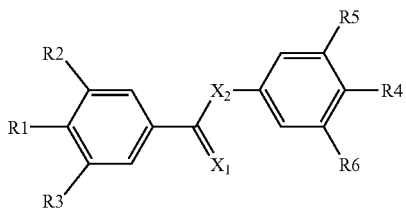

where either or both benzenes can be substituted with pyrazine, pyrimidine piperazine, morpholine, cyclohexane, piperizine or pyridine; R1 is a halogen such as bromine (Br), chlorine (Cl), fluorine (F), Iodine (I), amino ($NH_2$), nitro ($NO_2$), hydroxy (OH)O-methyl ($OCH_3$) methyl ($CH_3$) or hydrogen (H), R2, R3, R4, R5 and/or R6 is bromine (Br), chlorine (Cl), fluorine (F), Iodine (I), amino ($NH_2$), nitro ($NO_2$), methyl ($CH_3$), O-Methyl ($OCH_3$), hydroxy (OH), $CH(CH_3)_2$, CHO, $CHOCH_3$, $O(CH_2)nCH_3$, $OCO(C_6H_{12})Cl$, $COOCH_3$ or hydrogen; X1 is nitrogen (NH), oxygen (O) or sulfate (S); X2 is oxygen (O) or sulfate (S). Illustrative embodiments are found in the drawings, especially in FIGS. 3, 4, 5 and 6, but compounds of the invention are not limited to these embodiments.

The invention provides compounds that, when administered to a cell, abrogate the G2 checkpoint, in particular the DNA-damage-induced G2 checkpoint, and kill or suppress cells with or without DNA-damaging treatment, wherein the compounds have the following general structure:

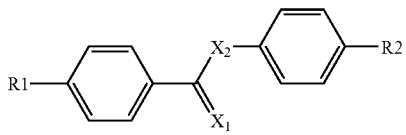

where either or both benzenes can be substituted with pyrazine, pyrimidine. piperazine, morpholine, cyclohexane, piperizine or pyridine; R1 is bromine (Br), chlorine (Cl), fluorine (F), Iodine (I), amino ($NH_2$), nitro ($NO_2$), hydroxy (OH)O-methyl ($OCH_3$) methyl ($CH_3$) or hydrogen (H), R2 is bromine (Br), chlorine (Cl), fluorine (F), Iodine (I), amino ($NH_2$), nitro ($NO_2$), methyl ($CH_3$), O-Methyl ($OCH_3$), hydroxy (OH), $CH(CH_3)_2$, CHO, $CHOCH_3$, $O(CH_2)nCH_3$, $OCO(C_6H_{12})Cl$, $COOCH_3$ or hydrogen; X1 is nitrogen (NH), oxygen (O) or sulfate (S); X2 is oxygen (O) or sulfate (S). Illustrative embodiments are found in the drawings, especially in FIGS. 3, 4, 5 and 6.

The invention provides compounds that abrogate the G2 checkpoint and/or suppress or kill cancer cells, with or without DNA-damaging treatment, wherein the compounds have the following general structure:

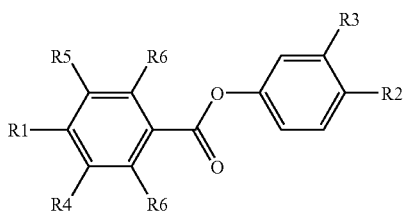

wherein substitution of different molecules at positions R1 to R6 affects the G2-checkpoint-abrogating activity of the resulting compounds. The following structure-activity relations have been determined At R1, bromine (Br) provides higher activity than chlorine (Cl), fluorine (F) or methyl ($CH_3$).

At R2, methyl ($CH_3$) or O-Methyl ($OCH_3$) provide higher activity than hydroxide (OH), bromine (Br), Cloride (Cl), $CH(CH_3)_2$, CHO, $CHOCH_3$, $O(CH_2)nCH_3$, $OCO(C_6H_{12})Cl$ or $COOCH_3$ or H.

At R3, methyl ($CH_3$) provided higher activity than H or O-Methyl ($OCH_3$).

At R4, bromine (Br), fluorine (F), chlorine (Cl), or H can be used.

At R5, bromine (Br), fluorine (F), chlorine (Cl), or H can be used.

At R6, bromine (Br), fluorine (F), chlorine (Cl), or H can be used.

The foregoing list is merely illustrative and not exhaustive. Illustrative embodiments are found in FIGS. 3, 4, 5, and 6. One of skill in the art can make additional substitutions and activity determinations according to the teachings of the present disclosure, to obtain additional compounds of the invention. It is understood by one of skill in the art that, although certain substitutions have been observed to produce structures with higher activity than other structures with respect to DNA-damage-induced G2 checkpoint abrogation, the invention provides compounds with all substitutions and all levels of activity. For a particular embodiment, one of skill will consider multiple factors in selecting a compound of the invention for use in that embodiment, in addition to the activity of a compound against a particular target. One of skill in the art will consider activity of the compound, availability, stability, ease or efficiency of synthesis, suitability for formulation in a pharmaceutical composition, drugability, interaction with other compounds in vivo, ex vivo, or in vitro, ability to kill cells, ability to suppress growth of cells, effects on normal cells, and other activities.

The invention provides compounds that abrogate the G2 checkpoint, in particular compounds that selectively abrogate the DNA-damage-induced cell cycle G2 checkpoint. Compounds are provided that selectively abrogate the DNA-damage-induced cell cycle G2 checkpoint in G1 checkpoint-defective cells such as cancer cells, and selectively abrogate the DNA-damage-induced G2 checkpoint in cells treated with DNA-damaging agents. The invention provides compounds that sensitize cancer cells to DNA-damaging treatments. Further provided are compounds that inhibit xenograft tumor growth, alone or in combination with anti-cancer agents. The invention provides compounds that suppress colony formation in vitro in cancer cells, alone or in combination with anti-cancer agents. In particular, the invention provides compounds that abrogate the G2 checkpoint and/or suppress or kill cancer cells, with or without DNA-damaging treatment, including but not limited to:

CDBC004: 4-Chloro-benzoic acid 4-methoxy-phenyl ester
CBDC401: 4-Chloro-benzoic acid p-tolyl ester
CBDC402: 4-Bromo-benzoic acid p-tolyl ester
CBDC403: 3,4,5-Trifluoro-benzoic acid p-toly 1 ester
CBDC404: 4-Fluoro-benzoic acid 4-bromo-pheny 1 ester; compound with ethane
CBDC405: 3,4-Dichloro-benzoic acid p-tolyl ester; compound with ethane
CBDC406: 2,4-Dichloro-benzoic acid p-tolyl ester; compound with ethane CBDC407: 4-Fluoro-benzoic acid p-tolyl ester; compound with ethane CBDC408: 2,3,4,5,6-Pentafluoro-benzoic acid p-tolyl ester; compound with ethane CBDC409: 4-Chloro-benzoic acid 3,4-dimethyl-phenyl ester; compound with ethane CBDC410: 4-Chloro-benzoic acid 4-hydroxy-phenyl ester; compound with ethane CBDC411: 4-Fluoro-benzoic acid 4-hydroxy-phenyl ester; compound with ethane CBDC412: 4-Bromo-benzoic acid 4-fluoro-phenyl ester CBDC413: 4-Bromo-benzoic acid 4-trifluoromethyl-phenyl ester CBDC414: 4-Bromo-benzoic acid 4-hydroxy-phenyl ester CBDC415: 4-Bromo-benzoic acid 4-trifluoromethoxy-phenyl ester CBDC418: 4-Bromo-benzoic acid 6-methyl-pyridin-3-yl ester CBDC440: 4-Bromo-thiobenzoic acid O-p-tolyl ester CBDC441: 4-Bromo-dithiobenzoic acid p-tolyl ester CBDC442: 4-Bromo-thiobenzoic acid S-p-tolyl ester Structures of these compounds are provided herein in FIGS. 3, 4, 5, and 6, and in the claims.

Figure 2:
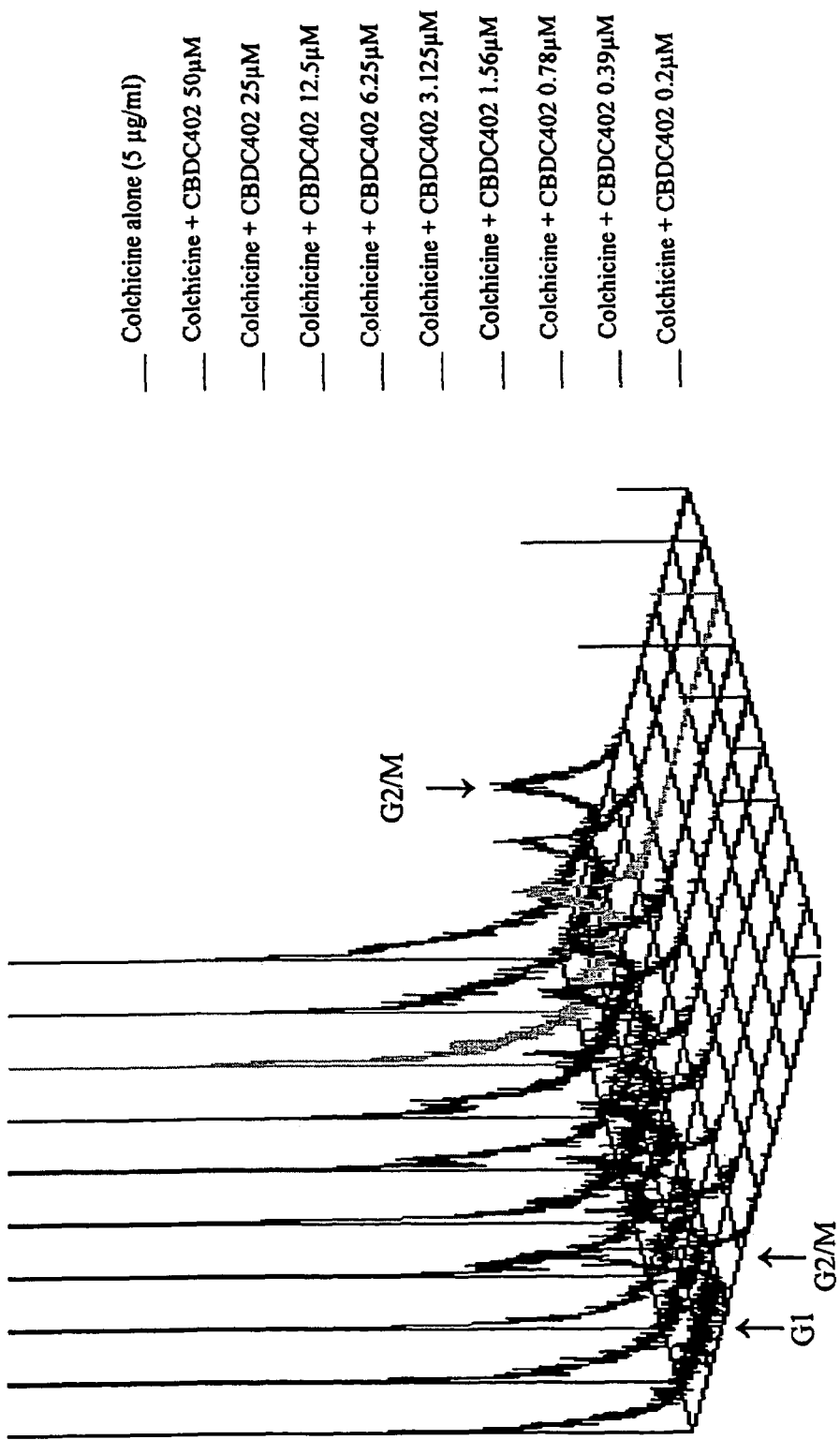
FIG. 2 shows the results of flow cytometry analysis of the DNA content of the Jurkat cells after the treatment with colchicine (5 ug/ml), or colchicine plus CBDC402 at various concentrations (0.2, 0.39, 0.78, 1.56, 3.125, 6.25, 12.5, 25 and 50 ug/ml) for 24 hrs.

The invention provides compositions that selectively abrogate the DNA-damage-induced cell cycle checkpoint. In one embodiment, compound CBDC402 selectively abrogated the DNA-damage-induced cell cycle G2 checkpoint in G1-checkpoint-defective cancer cells, as described below in Example 1. Treatment of Jurkat cells (human T-cell leukemia-derived cell line) with bleomycin, a DNA-damaging agent used as an anti-cancer agent, resulted in accumulation of cells in the G2/M phase, indicating G2 cell cycle arrest due to bleomycin-induced DNA damage. CBDC402 abolished the bleomycin-induced accumulation of cells in G2/M in a dose-dependent manner (FIG. 1). Colchicine does not induce G2 cell cycle arrest, and in another embodiment, CBDC402 did not inhibit colchicine-induced accumulation of cells in G2/M phase cells at any CBDC402 concentration (FIG. 2). Thus, CBDC402 selectively abrogated the DNA-damage-induced cell cycle checkpoint.

The invention provides compositions that abrogate DNA-damage-induced G2 checkpoint when administered to a cell. In various embodiments, compounds CBDC004, CBDC402, CBDC403, CBDC404, CBDC405, CBDC406, CBDC407, CBDC408, CBDC409, CBDC410 and CBDC411 abrogated the G2 cell cycle checkpoint in bleomycin-treated Jurkat cells in a dose-dependent manner (FIG. 3a). A dose-response curve for G2 checkpoint abrogation by various CBDC compounds showed that CBDC402 showed the highest activity in this embodiment, and all CBDC compounds tested were capable of abrogating G2 cell cycle checkpoint at the highest concentration (50 μg/ml). The structures corresponding to different levels of activity are shown in FIG. 3b; the CBDC designation corresponding to the structures disclosed in FIG. 3b can be found by reference to FIG. 4.

Figure 5:
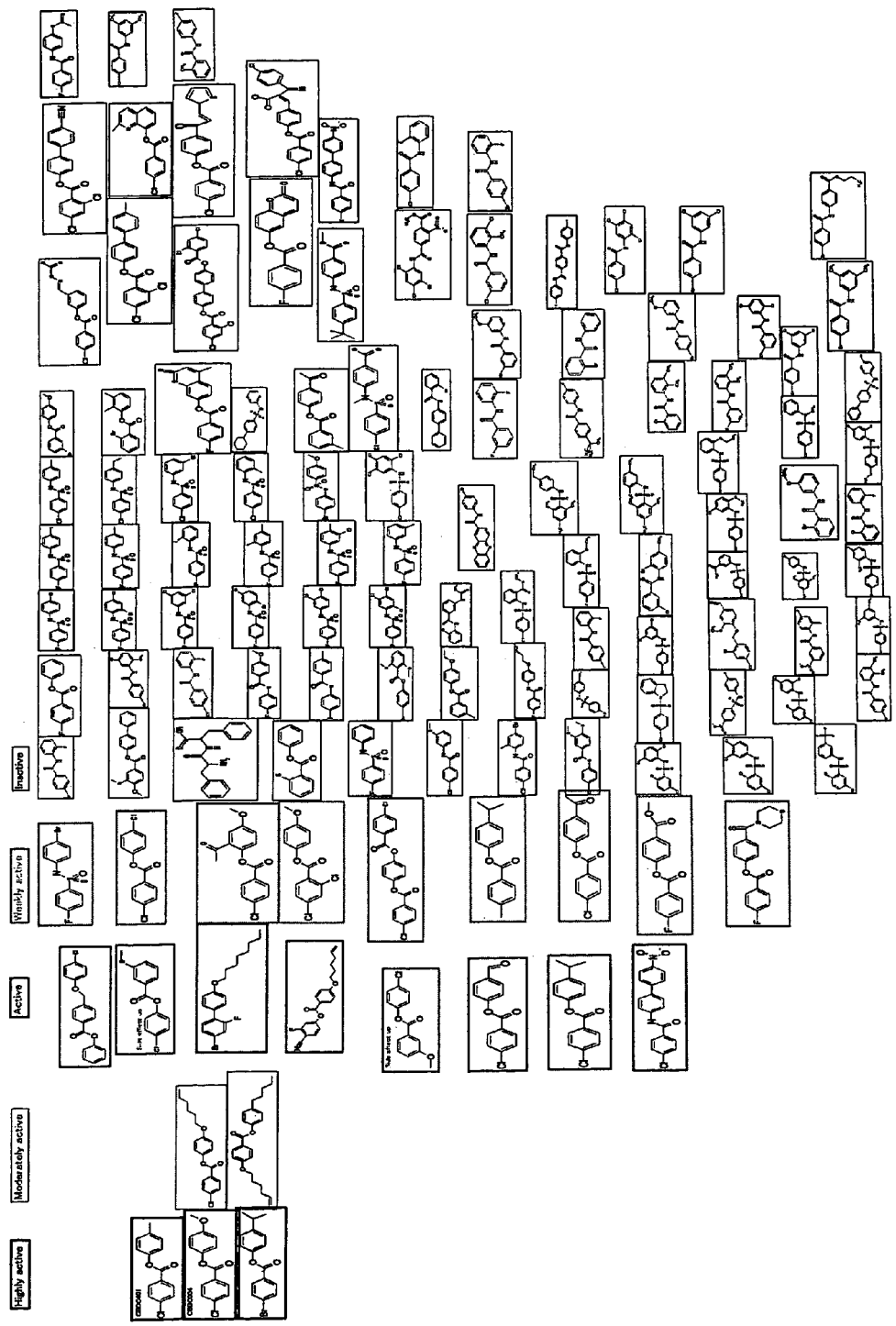
FIG. 5 shows the structure and relative activities of certain CBDC compounds.
Figure 6:
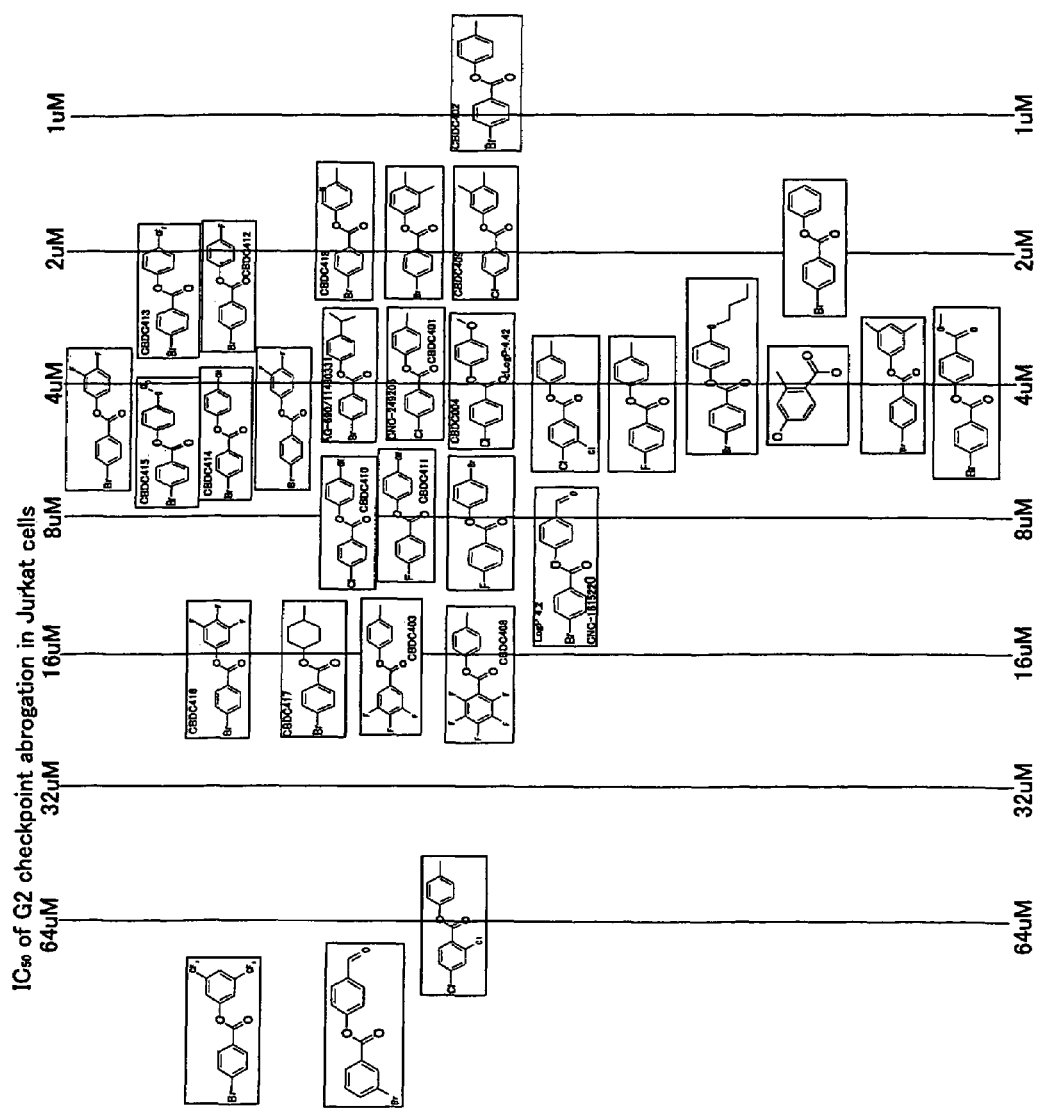
FIG. 6 shows the $IC_{50}$ values for G2 checkpoint abrogation by certain CBDC compounds.

The method provides compositions with different G2-checkpoint-abrogating activities, and further provides methods for determining these activities. In additional embodiments, CBDC compounds were tested for their G2 checkpoint abrogating activity. CBDC compounds were ranked as highly active; moderately active; active; weakly active; and inactive, as shown in FIG. 5. The $IC_{50}$ of G2 checkpoint abrogation in Jurkat cells was determined by dose-response studies carried out as described above activity and ranked according to their activity, as shown in FIG. 6. In FIGS. 5 and 6, CBDC compounds are fully disclosed by disclosure of their chemical structures, and in some entries, the CBDC compounds are additionally identified by a CBDC designation number.

The invention provides compositiions that abrogate the DNA-damage-induced G2 checkpoint induced by a variety of DNA-damaging agents. In one embodiment, compound CBDC004 abrogated the DNA-damage-induced G2 checkpoint activated by various anti-cancer agents. Human cancer cells (HCT116 human colon carcinoma cells) were treated with bleomycin, adriamycin, camptothecin, or cisplatin (CDDP), with or without compound CBDC004. Each of these anti-cancer agents induced an accumulation of cells at cell cycle G2/M, and co-incubation with CBDC004 reduced the number of cells at G2/M, indicating that CBDC004 had abrogated the DNA-damage-induced G2 checkpoint activated by bleomycin, adriamycin, camptothecin, or cisplatin.

Figure 8:
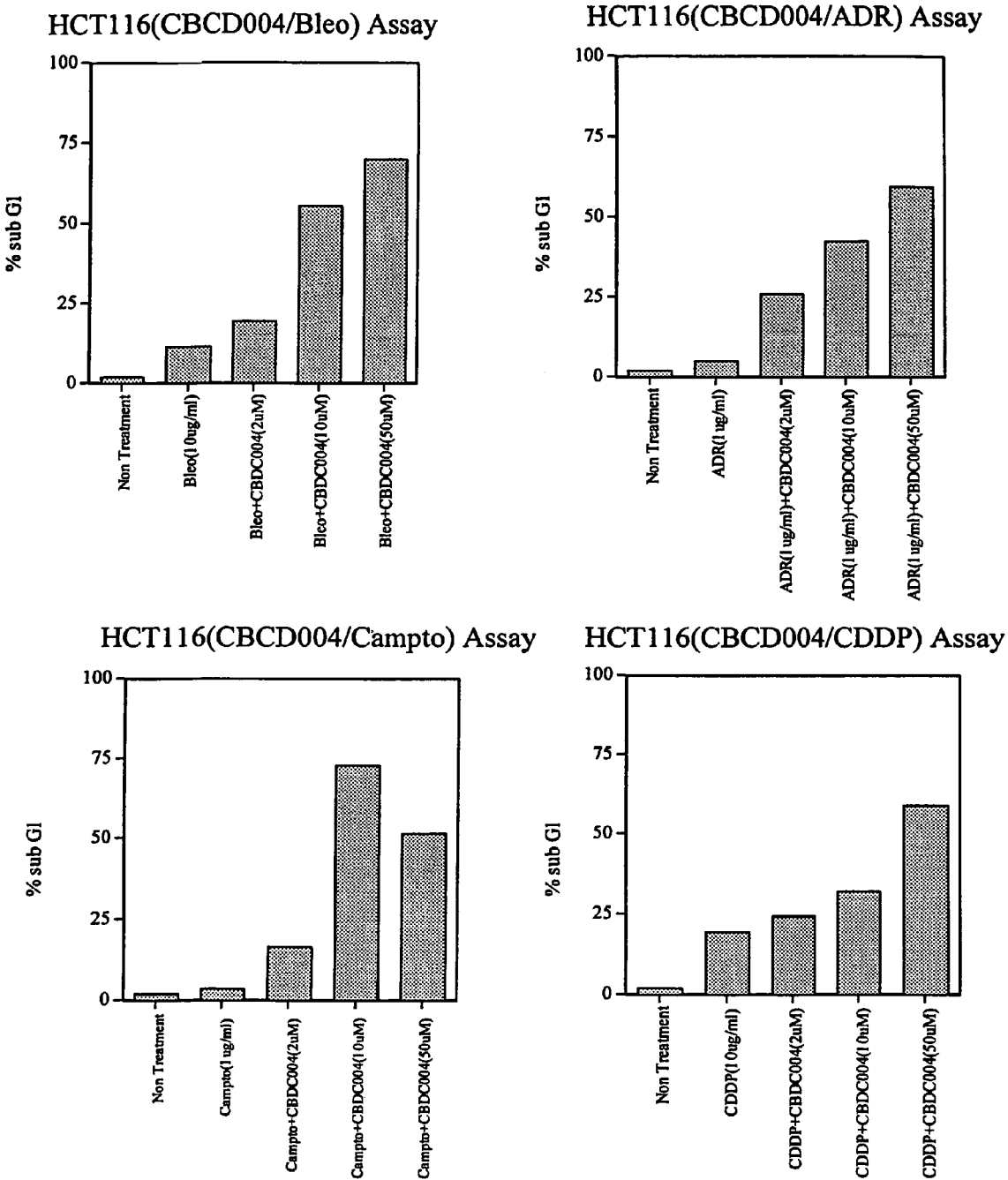
FIG. 8 shows the results of flow cytometry analysis of cytoxicity results (% subG1 population) for HCT116 cells treated with bleomycin (10 ug/ml), adriamycin (1 ug/ml), camptothecine (1 ug/ml) or cisplatin (CDDP, 10 ug/ml), and within each treatment regime, cells were treated with no CBDC004, or 2 uM, 10 uM, or 50 uM CBDC004; the subG1 population was determined by staining cells with Krishan's solution.

The invention provides compositions and methods for sensitizing cells to DNA-damaging treatments. In yet another embodiment, CBDC004 sensitized human cells to the cytotoxic effects of various DNA-damaging treatments that are used as anti-cancer agents. Human cancer cells (HCT116 cells) were treated with bleomycin, adriamycin, canptothecine or cisplatin, with or without CBDC004, and the number of dead cells was measured after the treatment. CBDC004 sensitized the cells to the cytotoxic effects of each DNA-damaging treatment (FIG. 8). Administering compounds of the present invention to cells sensitizes the cells to DNA-damaging treatments, making the DNA-damaging treatments more effective.

The invention provides compositions and methods for inhibiting growth of xenograft tumors. In another embodiment, CBDC402 inhibited growth of xenograft tumors. After HCT-116 human colon carcinoma cells were implanted subcutaneously in Severe Combined Immunodeficiency (SCID) mice, various compounds were administered and tumor growth was monitored. CBDC402 alone gave a slight reduction in tumor growth, and combinations of CBDC402 plus CPT-11 (CAMPTOSAR®, Irinotecan, a topoisomerase inhibitor) significantly reduced or inhibited tumor growth.

The invention provides compositions and methods for treating cells with proliferative disorders. In particular, the invention provides compounds and methods for inhibiting various aspects of cells having proliferative disorders, including inhibiting colony formation by cancer cells in vitro. Compounds of the invention inhibited colony formation by cancer cells in vitro, alone or in combination with an anti-cancer agent. In one embodiment, MK-45 cells from a human gastric cancer derived cell line, seeded into multiwell plates, were treated with CBDC402, CBDC412, CBDC413, and CBDC418. Treatment with CBDC402 alone caused significant suppression of colony formation by MK-45 cells, and treatment with CBDC412 caused a slight suppression of colony formation. In an embodiment that also included CPT-11, addition of CBDC402 appeared to augment the effect of CPT-11, resulting in almost complete suppression of colony formation.

Figure 10:
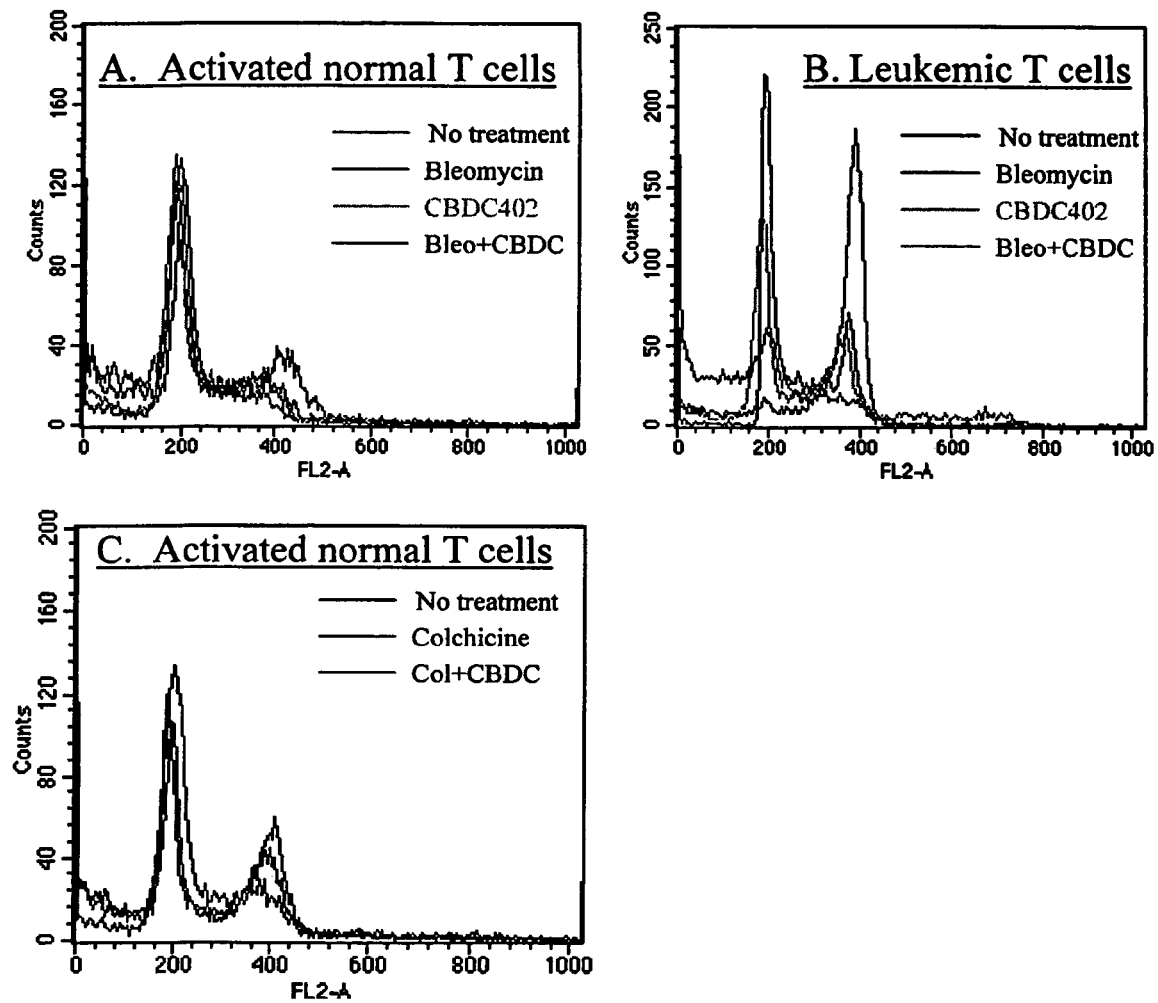
FIG. 10a-c shows results of flow cytometry analysis showing CBDC402 specifically abrogates the DNA-damage-induced cell cycle G2 checkpoint.

The invention provides compositions and methods to selectively abrogate the DNA-damage-induced G2 checkpoint without affecting the M checkpoint. In one embodiment, CBDC402 selectively abrogates the DNA-damage-induced G2 checkpoint. Bleomycin induced a moderate increase in the accumulation of activated normal T cells in G2 phase (FIG. 10a), and induced a large accumulation of cells in Jurkat cells (leukemic T cells) at G2 phase (FIG. 10b). CBDC abolished the bleomycin-induced increase of cells in G2 phase in both cell lines (FIG. 10a,b). When activated normal T cells received were treated with colchicine, which caused an accumulation of cells in M phase, and CBDC402 did not affect the colchicine-induced increase of activated normal T cells at M phase. This embodiment demonstrates that CBDC402 selectively abrogates the G2 cell cycle checkoint and not the not M phase checkpoint.

The invention provides methods for synthesizing compounds of the invention. In one embodiment, CBDC 412 (4-bromo-benzoic acid 4-fluoro-phenyl ester) is synthesized as described below. In one embodiment, ten ml of dioxane, 5 mmol (1.1 g) of 4-bromo-benzoic acid chlorine, and 5 mmol (0.56 g) of 4-fluoro-phenol were added to 50 ml four-mouth-flask sequentially and dissolved at room temperature. Triethylamine dissolved in dioxane was slowly dripped into this solution and the solution was stirred for three hours at room temperature. The precipitated crystals were filtered and extracted with benzene. The extracted solution was washed with sodium hydrocarbonate several times, magnesium anhydrate was added, and the resulting solution was dried and filtered. The solution was distilled under low pressure and crystallized. The row crystals were yellowish-white, weighing 1.37 g. A portion of this crystal (0.5 g) was dissolved in benzene and purified with 10 g of silica gel. The purified product was white, and the purity was confirmed to 99.93% by liquid chromatography (LC). The structure was confirmed by NMR (see, Example 6).

Screening

The invention provides compositions and methods for screening for potential therapeutic compounds ("test compounds" or "candidate compounds") to inhibit or abrogate the G2 checkpoint. Assay formats that can be used for screening are well known. For a general description of different formats for binding assays, see, e.g., BASIC AND CLINICAL IMMUNOLOGY, 7th Ed., Stiles and Terr, eds.(1991); ENZYME IMMUNOASSAY, Maggio, ed., CRC Press, Boca Raton, Fla. (1980); and "Practice and Theory of Enzyme Immunoassays" in Tijssen, LABORATORY TECHNIQUES IN BIOCHEMISTRY AND MOLECULAR BIOLOGY, Elsevier Science Publishers, B.V. Amsterdam (1985).

Targets

Subjects appropriate for treatment include those currently undergoing or are candidates for treatment for a proliferative or differentiative disorder or (e.g., anti-tumor therapy). Additional candidate subjects include, for example, subjects at risk of developing a cell proliferative disorder. The invention methods are therefore applicable to treating a subject who is at risk of developing a cell proliferative disorder but who has not yet exhibited overt symptoms of the disorder. At risk subjects can be identified as having a genetic predisposition or family history to developing a cell proliferative disorder. For example, subjects having an activated oncogene or having a mutation or deletion of a tumor suppressor gene are candidate subjects. At risk subjects can therefore be identified using routine genetic screening for the presence of the genetic lesion, or inquiry into the subjects' family history to establish that they are at risk of the disorder. A particular example of an at risk subject would be one with a family history or other genetic characteristic indicating predisposition to a cancer in which the neoplastic or drug-resistant neoplastic cells express CD40. A particular specific example of a genetic disease is retinoblastoma, which is caused by a defect in the Rb tumor suppressor gene.

Typically an "effective amount" or "sufficient amount" of a compound of the invention is administered, where that is an amount sufficient to produce the desired affect. Effective amounts therefore are determined by measuring one or more of: decreasing cell proliferation, decreasing numbers of cells, inhibiting increased proliferation, inhibiting increased numbers of cells, increasing apoptosis, or decreasing survival, of at least a portion of the cells comprising the proliferating cells (e.g., at least some of the target cells). Thus, for example, where it is desired to inhibit cell proliferation, an effective amount will be an amount that detectably decreases cell proliferation or numbers of proliferating cells, or increases cell apoptosis or decreases cell survival. The amount can therefore be sufficient to reduce target cell numbers, stabilize target cell numbers or inhibit increases in target cell numbers. For example, where the disorder comprises a solid tumor, reducing tumor size, stabilizing tumor size, or preventing further growth of the tumor, of at least a portion of the tumor (e.g. inhibiting growth of 5-10% of the cells, or 10-20% or more of the cells comprising the tumor mass) is a satisfactory clinical endpoint. Where the disorder comprises a liquid tumor, reducing numbers of tumor cells, stabilizing tumor cell numbers or inhibiting further increases in tumor cell numbers, of at least a subpopulation of the tumor cells (e.g. inhibiting growth of 5-10% of the cells, or 10-20% or more of the cells) is a satisfactory clinical endpoint.

In addition, amounts considered effective can prevent or inhibit progression of the condition or disorder. For example, certain tumors as they progress become increasingly aggressive, including progressing to metastatic forms. Thus, amounts also considered effective would result in reducing or preventing the tumors from becoming increasingly aggressive or from metastasizing. Accordingly, inhibiting or preventing a worsening of the disorder or condition, i.e., stabilizing the condition is an additional satisfactory clinical endpoint.

Examination of a biological sample containing a liquid tumor (e.g., blood or a tissue sample), can establish whether tumor cell mass or numbers have been reduced, or inhibition of tumor cell proliferation has occurred. For a solid tumor, invasive and non-invasive imaging methods can ascertain a reduction in tumor size, or inhibiting increases in the tumor size. Decreasing counts of receptor of a receptor positive tumor, can be used to assess reduction or inhibition of tumor cell proliferation. Amounts of hormone of a hormone producing tumor, e.g., breast, testicular, or ovarian cancers, can be used to assess a reduction or inhibition of proliferation of the tumor.

Effective amounts can also objectively or subjectively reduce or decrease the severity or frequency of symptoms associated with the disorder or condition. For example, an amount of an invention compound that reduces pain, nausea or other discomfort, or increases appetite or subjective well being is a satisfactory clinical endpoint.

Effective amounts also include a reduction of the amount (e.g., dosage) or frequency of treatment with another protocol, which is considered a satisfactory clinical endpoint. For example, a cancer patient treated with an invention compound may require less nucleic acid damaging treatment in order to inhibit cancer cell proliferation. In this example, an effective amount would include an amount that reduces the dosage frequency or amount of a nucleic acid damaging agent that the subject is administered in comparison to the dosage frequency or amount administered without treatment with a compound of the invention.

Methods of the invention that lead to an improvement in the subject's condition or a therapeutic benefit may be relatively short in duration, e.g., the improvement may last several hours, days or weeks, or extend over a longer period of time, e.g., months or years. An effective amount need not be a complete ablation of any or all symptoms of the condition or disorder. Thus, a satisfactory clinical endpoint for an effective amount is achieved when there is a subjective or objective improvement in the subjects' condition as determined using any of the foregoing criteria or other criteria known in the art appropriate for determining the status of the disorder or condition, over a short or long period of time. An amount effective to provide one or more beneficial effects, as described herein or known in the art, is referred to as an "improvement" of the subject's condition or "therapeutic benefit" to the subject.

An effective amount of an invention compound can be determined based upon animal studies or optionally in human clinical trials. The skilled artisan will appreciate the various factors that may influence the dosage and timing required to treat a particular subject including, for example, the general health, age, or gender of the subject, the severity or stage of the disorder or condition, previous treatments, susceptibility to undesirable side effects, clinical outcome desired and the presence of other disorders or conditions. Such factors may influence the dosage and timing required to provide an amount sufficient for therapeutic benefit. The dosage regimen also takes into consideration the pharmacokinetics, i.e., the pharmaceutical composition's rate of absorption, bioavailability, metabolism, and clearance. In addition, doses or treatment protocols may be specifically tailored to the subject or modified based on pharmacogenomic data.

Cells that may be treated with the compounds of the invention include any cell whose proliferation it is desired to inhibit or prevent in vitro, ex vivo or in vivo. Certain target cells exhibit a shorter than normal cell cycle G1 checkpoint time or have an impaired cell cycle G1 checkpoint such that the cells exit the G1 checkpoint before enough time has passed to complete nucleic acid repair. Candidate cells can also be identified by contacting a test cell with an invention compound alone, or in combination with a DNA-damaging treatment, and determining if the contacted cell exhibits decreased proliferation or increased cell death, in particular apoptosis or mitotic catastrophe.

Invention compounds are therefore useful for inhibiting cell proliferation in vitro, ex vivo and in vivo. As such, subjects having or at risk of having a disorder or physiological condition characterized by abnormal or undesirable or unwanted cell proliferation or cell survival, or abnormal or deficient cell differentiation, can be treated with a compound of the invention alone or in combination with a treatment that directly or indirectly causes DNA damage, or in combination with an anti-proliferative treatment.

Thus, in accordance with the invention, there are provided methods for inhibiting cell proliferation, methods for increasing sensitivity of a cell to a DNA-damaging agent or treatment and methods for increasing nucleic acid damage to a cell in vitro, ex vivo and in vivo. In one embodiment, a method includes contacting a cell (e.g., a cultured cell or a cell present in a subject) with an amount of compound of the invention sufficient to abrogate the G2 checkpoint. In another embodiment, a method includes contacting the cell with an amount of a compound of the invention sufficient to increase sensitivity of the cell to a DNA-damaging agent or treatment. In yet another embodiment, a method includes contacting a cell with an amount of a compound of the invention sufficient to increase nucleic acid damage of the cell. In various aspects, a method further includes contacting the cell with a DNA-damaging agent or exposing the cell to a DNA-damaging treatment.

Further provided are methods of treating a cell proliferative disorder or differentiative disorder in a subject, including conditions characterized by undesirable or unwanted cell proliferation or cell survival, conditions characterized by deficient or aberrant apoptosis, conditions characterized by aberrant or deficient cell survival, as well as conditions characterized by aberrant or deficient cell differentiation. In one embodiment, a method includes administering to a subject having or at risk of having a cell proliferative disorder, an amount of a compound of the invention effective to treat the cell proliferative disorder. In one aspect, the amount is sufficient to improve the subject's condition. In particular aspects, the improvement includes, in at least a portion of the target cells (e.g., abnormally proliferating cells), decreased cell proliferation, decreased numbers of cells, inhibiting increases in the number of cells, increased apoptosis, or decreased survival. In yet another aspect, a compound of the invention is administered to a subject prior to, contemporaneously with, or after administering a treatment that inhibits cell proliferation. In additional particular aspects, at least a part of the cells of the cell proliferative disorder are located in blood, breast, lung, thyroid, head or neck, brain, lymph, gastrointestinal tract, genito-urinary tract, kidney, pancreas, liver, bone, muscle, or skin.

In another embodiment, a method includes administering an amount of compound of the invention to a subject to treat a solid tumor. In yet another embodiment, a method includes administering an amount of compound of the invention to the subject to treat a liquid tumor. In various aspects, the subject having the tumor is administered with an compound of the invention prior to, contemporaneously with, or after another anti-tumor therapy.

Use of Compounds of the Invention to Treat Proliferative or Differentiative Disorders.

Proliferative or differentiative disorders amenable to treatment using compositions and methods provided herein include diseases and non-pathological physiological conditions, both benign and neoplastic, characterized by abnormal or undesirable cell numbers, cell growth or cell survival. Such disorders or conditions may therefore constitute a disease state and include all types of cancerous growths or oncogenic processes, metastatic tissues or malignantly transformed cells, tissues, or organs, or may be non-pathologic, i.e., a deviation from normal but which is not typically associated with disease. A specific example of a non-pathologic condition that may be treated in accordance with the invention is tissue re-growth from wound repair that results in scarring.

Cells comprising the proliferative or differentiative disorder may be aggregated in a cell mass or be dispersed. The term "solid tumor" refers to neoplasias or metastases that typically aggregate together and form a mass. Particular examples include visceral tumors such as gastric or colon cancer, hepatomas, venal carcinomas, lung and brain tumors/cancers. A "liquid tumor" refers to neoplasias of the haematopoetic system, such as lymphomas, myelomas and leukemias, or neoplasias that are diffuse in nature, as they do not typically form a solid mass. Particular examples of leukemias include acute and chronic lymphoblastic, myeolblasitc and multiple myeloma.

Such disorders include neoplasms or cancers, which can affect virtually any cell or tissue type, e.g., carcinoma, sarcoma, melanoma, metastatic disorders or haematopoietic neoplastic disorders. A metastatic tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, etc.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the cervix, lung, prostate, breast, head and neck, colon, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, and fibrosarcoma.

As used herein, the term "haematopoietic proliferative disorder" means a disease involving hyperplastic/neoplastic cells of haematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Treatments for use in combination with compounds of the invention include any anti-proliferative, DNA-damaging, or anti-tumor treatment as disclosed herein or known in the art. For example, an anti-cell proliferative or anti-tumor treatment may comprise radiation treatment or surgical resection optionally in combination with drug treatment. The treatment may comprise administration of a chemical substance, such as a radioisotope, a drug, such as a chemotherapeutic agent, or genetic therapy, such as an anti-oncogene (e.g., Rb, DCC, p53, etc.), a dominant negative oncogene or an antisense to an oncogene. The compounds can be administered prior to, contemporaneously with or following other treatment protocols. For example, a candidate subject for anti-cell proliferative therapy (e.g., radiation therapy, chemotherapy, gene therapy, surgical resection, etc.) can be administered an invention compound prior to initiating the anti-cell proliferative therapy. Thus, prophylactic treatment methods are provided.

Combinatorial Chemical Libraries

Combinatorial chemical libraries are one means to assist in the generation of new chemical compound leads, i.e., compounds that inhibit or abrogate the G2 cell cycle arrest checkpoint. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks results in the theoretical synthesis of 100 million tetrameric compounds or 10 billion pentameric compounds. Preparation and screening of combinatorial chemical libraries are well known to those of skill in the art, see, e.g., U.S. Pat. Nos. 6,004,617; 5,985,356. Such combinatorial chemical libraries include, but are not limited to, peptide libraries (see, e.g., U.S. Pat. No. 5,010,175; Furka (1991) Int. J. Pept. Prot. Res., 37: 487-493, Houghton et al. (1991) Nature, 354: 84-88). Other chemistries for generating chemical diversity libraries include, but are not limited to: peptoids (see, e.g., WO 91/19735), encoded peptides (see, e.g., WO 93/20242), random bio oligomers (see, e.g., WO 92/00091), benzodiazepines (see, e.g., U.S. Pat. No. 5,288,514), diversomers such as hydantoins, benzodiazepines and dipeptides (see, e.g., Hobbs (1993) Proc. Nat. Acad. Sci. USA 90: 6909 6913), vinylogous polypeptides (see, e.g., Hagihara (1992) J. Amer. Chem. Soc. 114: 6568), non-peptidal peptidomimetics with a Beta D Glucose scaffolding (see, e.g., Hirschmann (1992) J. Amer. Chem. Soc. 114: 9217 9218), analogous organic syntheses of small compound libraries (see, e.g., Chen (1994) J. Amer. Chem. Soc. 116: 2661), oligocarbamates (see, e.g., Cho (1993) Science 261:1303), and/or peptidyl phosphonates (see, e.g., Campbell (1994) J. Org. Chem. 59: 658). See also Gordon (1994) J. Med. Chem. 37:1385; for nucleic acid libraries, peptide nucleic acid libraries, see, e.g., U.S. Pat. No. 5,539,083; for antibody libraries, see, e.g., Vaughn (1996) Nature Biotechnology 14:309-314; for carbohydrate libraries, see, e.g., Liang et al. (1996) Science 274: 1520-1522, U.S. Pat. No. 5,593,853; for small organic molecule libraries, see, e.g., for isoprenoids U.S. Pat. No. 5,569,588; for thiazolidinones and metathiazanones, U.S. Pat. No. 5,549,974; for pyrrolidines, U.S. Pat. Nos. 5,525,735 and 5,519,134; for morpholino compounds, U.S. Pat. No. 5,506,337; for benzodiazepines U.S. Pat. No. 5,288,514.

Devices for the preparation of combinatorial libraries are commercially available (see, e.g., U.S. Pat. Nos. 6,045,755; 5,792,431; 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of robotic systems have also been developed for solution phase chemistries. These systems include automated workstations, e.g., like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Formulation and Administration of Pharmaceutical Compositions

In one embodiment, the compounds of the invention are combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the compounds, or excipients or other stabilizers and/or buffers. Detergents can also used to stabilize or to increase or decrease the absorption of the pharmaceutical composition, including liposomal carriers. Pharmaceutically acceptable carriers and formulations for compounds as disclosed herein are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the compound of the invention and on its particular physio-chemical characteristics.

In one embodiment, a solution of at least one compound of the invention is dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chlorine, potassium chlorine, calcium chlorine, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of peptide in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chlorine, dried skim milk, glycerol, propylene glycol, water, ethanol.

Compounds of the invention, when administered orally, can be protected from digestion. This can be accomplished either by complexing the compound or compounds with a composition to render it resistant to acidic and enzymatic hydrolysis or by packaging the peptide or complex in an appropriately resistant carrier such as a liposome. Means of protecting compounds from digestion are well known in the art, see, e.g., Fix (1996) Pharm Res. 13:1760 1764; Samanen (1996) J. Pharm. Pharmacol. 48:119 135; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani (1996) "Systemic delivery of peptides and proteins across absorptive mucosae" Crit. Rev. Ther. Drug Carrier Syst. 13:85 184. For topical, transdermal administration, the agents are formulated into ointments, creams, salves, powders and gels. Transdermal delivery systems can also include, e.g., patches.

Compounds of the invention can also be administered in sustained delivery or sustained release mechanisms, which can deliver the formulation internally. For example, biodegradable microspheres or capsules or other biodegradeable polymer configurations capable of sustained delivery of a compound as disclosed herein can be included in the formulations of the invention (see, e.g., Putney (1998) Nat. Biotechnol. 16:153 157).

For inhalation, compounds of the invention can be delivered using any system known in the art, including dry powder aerosols, liquids delivery systems, air jet nebulizers, propellant systems, and the like. For example, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the complexes in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The compounds and compositions used in the methods of the invention can be delivered alone or as pharmaceutical compositions by any means known in the art, e.g., systemically, regionally, or locally (e.g., directly into, or directed to, a tumor); by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for preparing administrable compositions will be known or apparent to those skilled in the art and are described in detail in the scientific and patent literature, see e.g., Remington's. For a "regional effect," e.g., to focus on a specific organ, one mode of administration includes intra-arterial or intrathecal (IT) injections, e.g., to focus on a specific organ, e.g., brain and CNS (see e.g., Gurun (1997) Anesth Analg. 85:317 323). For example, intra-carotid artery injection if preferred where it is desired to deliver a peptide or polypeptide complex of the invention directly to the brain. Parenteral administration is a preferred route of delivery if a high systemic dosage is needed. Actual methods for preparing parenterally administrable compositions will be known or apparent to those skilled in the art and are described in detail, in e.g., Remington's,. See also, Bai (1997) J. Neuroimmunol. 80:65 75; Warren (1997) J. Neurol. Sci. 152:31 38; Tonegawa (1997) J. Exp. Med. 186:507 515.

In one embodiment, the pharmaceutical formulations comprising compounds of the invention are incorporated in lipid monolayers or bilayers, e.g., liposomes, see, e.g., U.S. Pat. Nos. 6,110,490; 6,096,716; 5,283,185; 5,279,833. Liposomal formulations can be by any means, including administration intravenously, transdermally (see, e.g., Vutla (1996) J. Pharm. Sci. 85:5 8), transmucosally, or orally. The invention also provides pharmaceutical preparations in which the peptides and/or complexes of the invention are incorporated within micelles and/or liposomes (see, e.g., Suntres (1994) J. Pharm. Pharmacol. 46:23 28; Woodle (1992) Pharm. Res. 9:260 265). Liposomes and liposomal formulations can be prepared according to standard methods and are also well known in the art, see, e.g., Remington's; Akimaru (1995) Cytokines Mol. Ther. 1:197 210; Alving (1995) Immunol. Rev. 145:5 31; Szoka (1980) Ann. Rev. Biophys. Bioeng. 9:467, U.S. Pat. Nos. 4,235,871, 4,501,728 and 4,837,028.

A pharmaceutically acceptable formulation can incorporate about 1% to 99.9% of active ingredient (e.g., a compound of the present invention). The pharmaceutical compositions can be sterilized by conventional, well-known sterilization techniques, or can be sterile filtered. Additional pharmaceutical formulations and delivery systems are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms, Technonic Publishing Co., Inc., Lancaster, Pa., (1993); and Poznansky et al., Drug Delivery Systems, R. L. Juliano, ed., Oxford, N.Y. (1980), pp. 253-315)

The pharmaceutical formulations can be packaged in unit dosage form for ease of administration and uniformity of dosage. "Unit dosage form" as used herein refers to physically discrete unitary dosages for administration to the subject to be treated; each unit contains a predetermined quantity of compound that produces a desired effect in combination with a pharmaceutical carrier or excipient.

The invention further provides kits including invention compounds and pharmaceutical formulations thereof, optionally packaged into suitable packaging material. A kit typically includes a label or packaging insert including a description of the components or instructions for use in vitro, in vivo, or ex vivo, of the components therein. A kit can contain a collection of such components, e.g., two or more invention compounds or an invention compound in combination with a nucleic acid damaging agent or an anti-proliferative agent.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions.

Kits of the invention therefore can additionally include labels or instructions for using the kit components in any method of the invention. Instructions can include instructions for practicing any of the methods of the invention described herein including treatment, detection, monitoring or diagnostic methods. Thus, for example, a kit can include an invention compound in a pack, or dispenser together with instructions for administering the compound in a treatment method of the invention. Instructions may additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

Invention kits can additionally include a buffering agent, or a preservative or a stabilizing agent in a pharmaceutical formulation. Each component of the kit can be enclosed within an individual container and all of the various containers can be within a single package. Invention kits can be designed for cold storage.

Treatment Regimens: Pharmacokinetics

The pharmaceutical compositions can be administered in a variety of unit dosage forms depending upon the method of administration. Dosages for typical pharmaceutical compositions are well known to those of skill in the art. Such dosages are typically advisorial in nature and are adjusted depending on the particular therapeutic context, patient tolerance, etc. The amount of compound or compounds of the invention that is adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton (1997) "Bioavailability and transport of peptides and peptide drugs into the brain" Peptides 18:1431 1439; Langer (1990) Science 249:1527-1533.

In therapeutic applications, compositions are administered to a patient suffering from a cancer in an amount sufficient to at least partially arrest the disease and/or its complications. For example, in one embodiment, a soluble pharmaceutical composition dosage for intravenous (IV) administration would be about 0.01 mg/hr to about 1.0 mg/hr administered over several hours (typically 1, 3, or 6 hours), which can be repeated for weeks with intermittent cycles. Considerably higher dosages (e.g., ranging up to about 10 mg/ml) can be used, particularly when the drug is administered to a secluded site and not into the blood stream, such as into a body cavity or into a lumen of an organ, e.g., the cerebrospinal fluid (CSF).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

EXAMPLES

The following examples are offered to illustrate, but not to limit the claimed invention.

Example 1

Selective Abrogation of DNA-Damage-Induced Cell Cycle G2 Checkpoint in G1 Checkpoint Defective Cells (Cancer Cells)

Chemicals and reagents. Bleomycin, adriamycin and colchicine were purchased from Wako Pure Chemical Co. (Osaka, Japan). These chemicals were dissolved in distilled $H_2O$ at 10 mg/ml and stored at 4° C. Cisplatin was purchased from Nihon Kayaku Co. (Tokyo, Japan), dissolved in distilled $H_2O$ at 5 mg/ml, and stored at 4° C. Camptothecine (Campto) was purchased from Sigma Chemical Co. (St. Louis, Mo.). Propidium iodine (PI) was purchased from Sigma. Phytohemagglutinin was purchased from Life Technologies, Inc. (Grand Island, N.Y.). Interleukin 2 (IL-2) was purchased from Hemagen Diagnostics Inc.

Cell culture. A human T-cell leukemia-derived cell line, Jurkat, was cultured in RPMI 1640 media (Sigma) supplemented with 10% fetal calf serum (IBL: Immuno-Biological Laboratories, Gunma, Japan) at 37° C./5% $CO_2$. A human colon cancer-derived cell line, HCT116, was cultured in McCoy's 5A Medium Modified (Gibco BRL) and supplemented with 10% fetal calf serum at 37° C./5% $CO_2$. Normal human peripheral blood lymphocytes were separated by Ficoll-Paque® (Pharmacia) and cultured in the presence of 0.1 μg/ml PHA and 1 μg/ml IL-2.

Cell-cycle analysis. The cell cycle status of the cells treated with compounds of the invention and/or bleomycin, adriamycin, colchicine, or cisplatin was analyzed by flow cytometry, essentially as described by Kawabe (1997) *Nature* 385:454-458. Briefly, two million cells were resuspended and incubated in 300 μl Krishan's solution (0.1% Sodium citrate, 50 μg/ml PI, 20 μg/ml RNase A and 0.5% NP-40) for 1 hr at 4° C. and analyzed by flow cytometry using a FACScan™ flow cytometer (Beckton Dickinson, Mountain View, Calif.) with the CELLQuest™ program (Beckton Dickinson).

CBDC402 Abolished Bleomycin-Induced Cell Cycle G2 Accumulation of Jurkat Cells.

Jurkat cells (a human T cell leukemia-derived cell line) were treated with bleomycin (40 μg/ml), or bleomycin plus compound CBDC402 (4-bromo-benzoic acid p-tolyl ester) at various concentrations (0.2, 0.39, 0.78, 1.56, 3.125, 6.25, 12.5, 25 and 50 μg/ml) for 24 hrs. DNA of treated Jurkat cells was stained with propidium iodine, and the cell cycle status of each cell was assessed by flow cytometry. As shown in FIG. 1, bleomycin treatment induced an accumulation of cells in cell cycle G2/M phase. CBDC402 treatment abolished the bleomycin-induced accumulation of G2/M cells in a dose-dependent manner.

M Phase Checkpoint in Jurkat Cells was not Abrogated by CBDC402 Treatment.

Jurkat cells were treated with colchicine (5 ug/ml), and colchicine plus the compound CBDC402 in various concentrations (0.2, 0.39, 0.78, 1.56, 3.125, 6.25, 12.5, 25 and 50 ug/ml) for 24 hrs. DNA of treated Jurkat cells was stained with propidium iodine, and the cell cycle status of each cell was assessed by flow cytometry. As shown in FIG. 2, colchicine treatment induced an accumulation of cells in G2/M phase cells, and CBDC402 did not abrogate this G2/M accumulation at any CBDC402 concentration.

Various CBDC Compounds Abrogated the Cell Cycle G2 Checkpoint.

Figure 3:
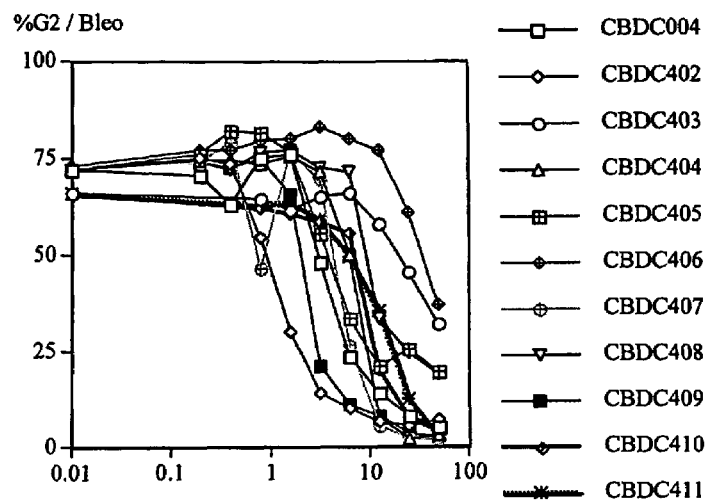
FIG. 3a-b shows activities of various CBDC compounds.
Figure 3:
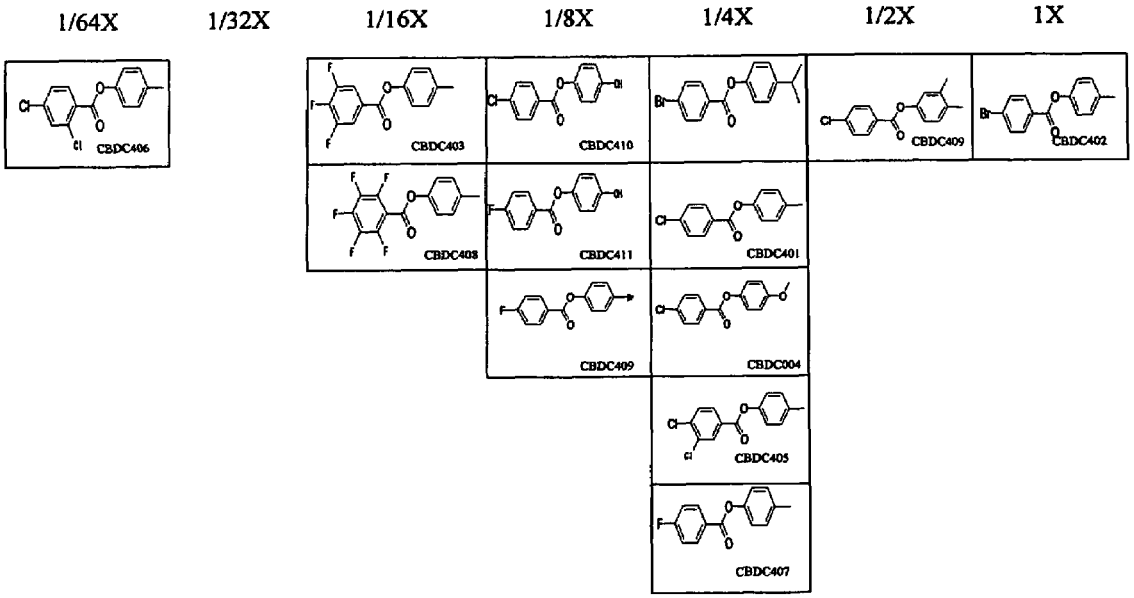
Figure 4:
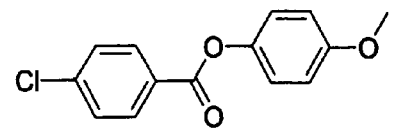
FIG. 4 shows the structures, chemical names, and CBDC codes for certain CBDC compounds.
Figure 4:
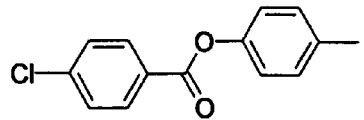
Figure 4:
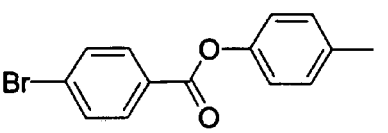
Figure 4:
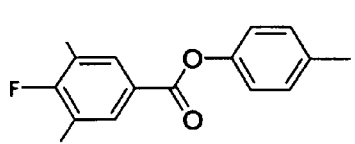
Figure 4:
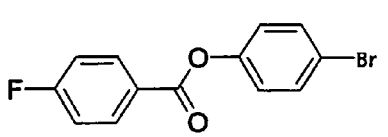
Figure 4:
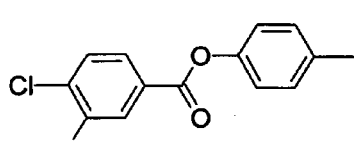
Figure 4:
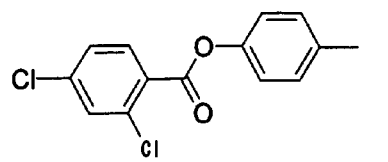
Figure 4:
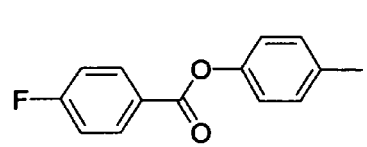

Jurkat cells were treated with bleomycin (40 ug/ml), and various CBDC compounds at 0.2, 0.39, 0.78, 1.56, 3.125, 6.25, 12.5, 25 and 50 ug/ml and cultured for 24 hrs. CBDC compounds 004, 402, 403, 404, 405, 406, 407, 408, 409, 410, and 411 were tested. Cells were harvested, DNA was stained with propidium iodine, and the percentage of cells in G2/M phase (% G2/M) was determined by flow cytometry. FIG. 3 shows the % G2/M cells that were detected for each concentration of each CBDC compound, providing a dose-response curve for G2 checkpoint abrogation by various CBDC compounds. CBDC402 showed the highest activity. All CBDC compounds tested abrogated G2 cell cycle checkpoint at the highest concentration (50 μg/ml). Structures of CBDC compounds tested in this experiment are shown in FIG. 4.

Additional CBDC compounds were tested for their G2 checkpoint abrogating activity as described above. As shown in FIG. 5, compounds were ranked as: highly active; moderately active; active; weakly active; and inactive. As shown in FIG. 6, the $IC_{50}$ of G2 checkpoint abrogation in Jurkat cells was determined by dose-response studies carried out as described above.

CBDC004 Abrogated Cell Cycle G2 Checkpoint Induced by Various Anti-Cancer Agents.

Figure 7:
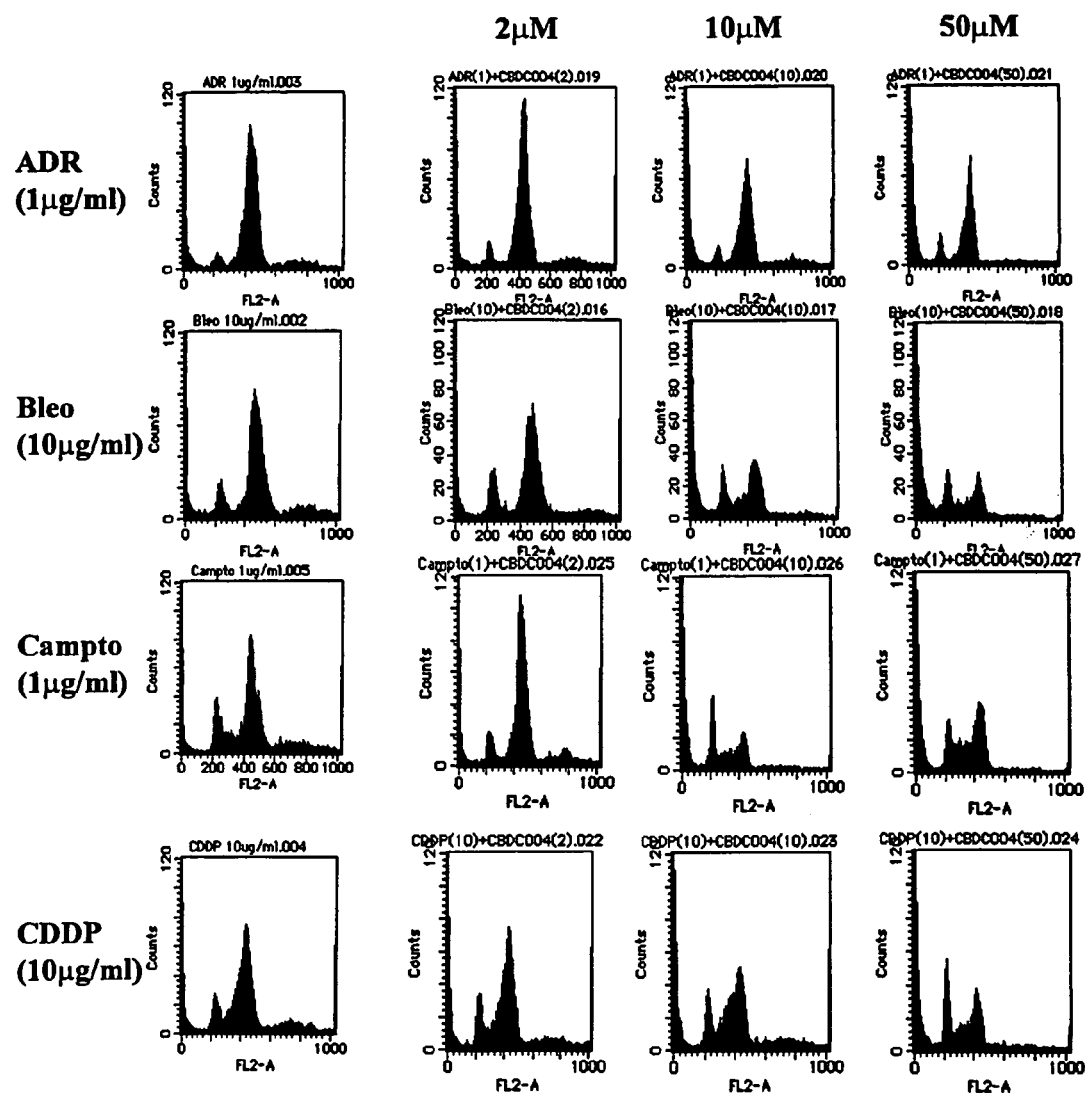
FIG. 7 shows the results of flow cytometry analysis of the DNA content of HCT116 cells after treatment with adriamycin (ADR), bleomycin (Bleo), comptothecin (Campto) and cisplatin (CDDP) for 24 hrs, after which time cells were treated with no CBDC004, or 2 uM, 10 uM, or 50 uM CBDC004.

HCT116 human colon carcinoma cells were treated with bleomycin (Bleo) at 10 μg/ml, or adriamycin (ADR) at 1 μg/ml, or camptothecin (Campto) at 10 μg/ml, or cisplatin (CDDP) at 2 μg/ml, and CBDC004 at 0, 2 μM, 10 μM, or 50 μM, for 24 hrs. DNA was stained with propidium iodine, and the cell cycle status of each cell was assessed by flow cytometry. As shown in FIG. 7, each of these anti-cancer agents induced an accumulation of cells at cell cycle G2/M, and co-incubation with CBDC004 reduced the number of cells at G2/M. This indicates that CBDC004 abrogated the G2 checkpoint activated by bleomycin, adriamycin, camptothecin, or cisplatin.

Example 2

Sensitization of Cancer Cells to DNA-Damaging Treatment

The cytotoxic activity of combination treatments were determined by analyzing subG1 population of HCT116 cells treated with bleomycin, adriamycine, canptothecine or cisplatin with or without CBDC004 at 2 μM, 10 μM, or 50 μM. The subG1 population was determined by staining HCT116 with Krishan's solution and analyzed by flow cytometer. The dead cells were identified on the basis of DNA content, and the percentage of cells in sub G1 (% subG1) was calculated. As shown in FIG. 8, bleomycin, adriamycine, canptothecine or cisplatin had a cytotoxic effect on HCT116 cells, and CBDC004 increased the cytotoxic activities of these anti-cancer agents in a dose dependent manner.

Example 3

CBDC402 Suppressed Xenograft Tumor Growth in SCID Mice

HCT-116 human colon carcinoma cells were implanted subcutaneously in Severe Combined Immunodeficiency (SCID) mice. Treatment was initiated when the primary tumors reached the size of 0.1 cm³ (7 or 8 mm, designated as Day1).

Figure 9:
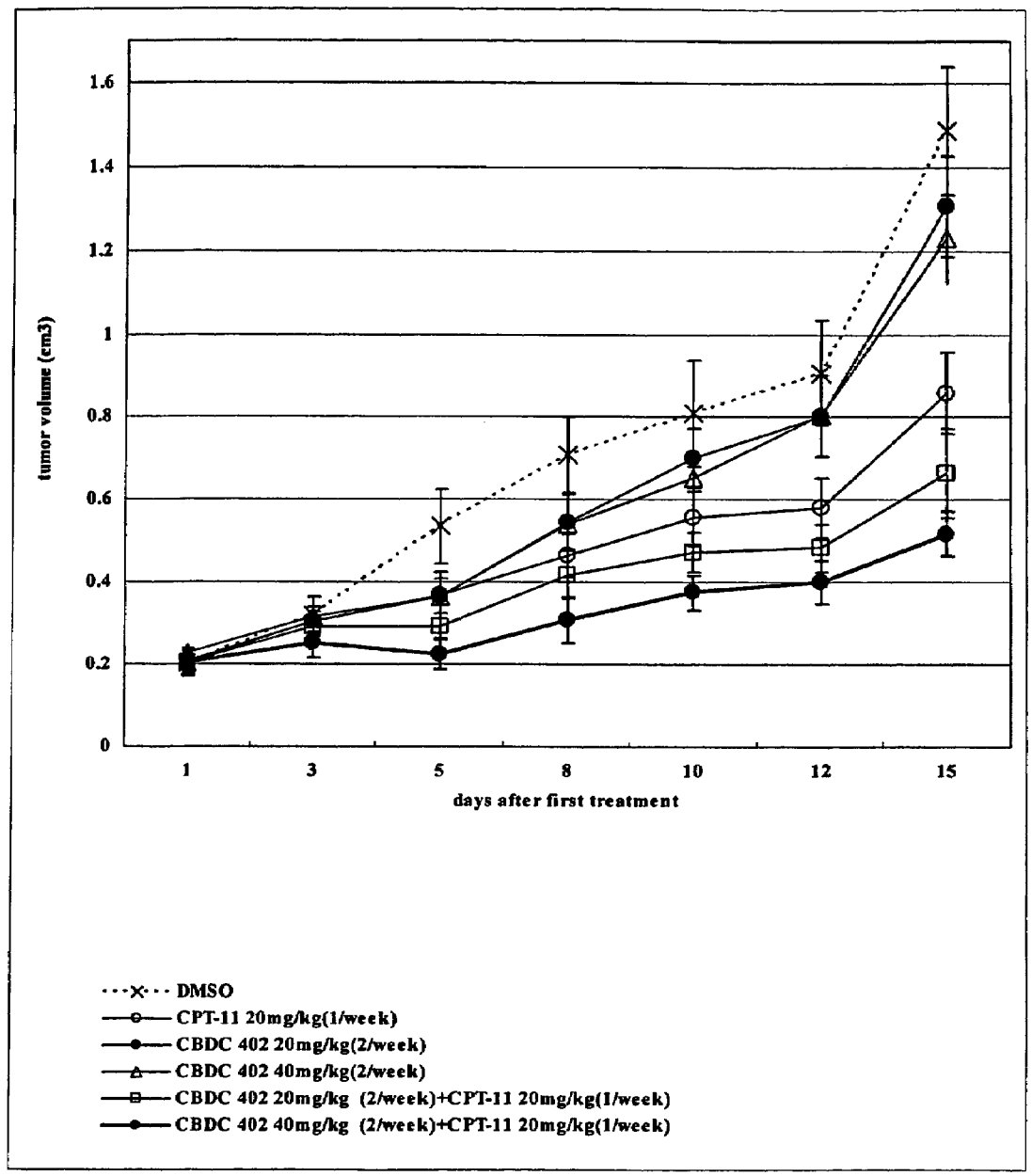
FIG. 9 shows the effect on tumor growth of CPT-11, CBDC402, or a combination of CPT-11 and CBDC402, where human colon cancer cell line HCT116 cells were subcutaneously implanted in SCID mice; mean tumor sizes for each treatment group were plotted (n=4) against the days after treatment.

Anti-cancer agent CPT-11 (CAMPTOSAR®), Irinotecan, a topoisomerase inhibitor) and CBDC402 were administered by intraperitoneal injection in the following treatment regimens: CPT-11 at 20 mg/kg once a week; CBDC402 at 20 mg/kg twice a week; CBDC402 at 40 mg/kg twice a week; CBDC402 at 20 mg/kg twice and week plus CPT-11 at 20 mg/kg once a week; and CBDC402 at 40 mg/kg twice a week plus CPT-11 at 20 mg/kg once a week. DMSO was administered as a control treatment. Tumor sizes were measured using calipers three times a week, and the volume was calculated using the formula; weight (mg)=[width (mm)$^2$×length (mm)]/2. Mean tumor sizes for each treatment group (n=4) were plotted against the days of treatment. As shown in FIG. 9, tumors in DMSO-treated control mice continued to grow, CBDC402 alone (both concentrations) gave a slight reduction in tumor growth, CPT-11 alone reduced tumor growth, and combinations of CBDC402 plus CPT-11 significantly reduced or inhibited tumor growth.

Example 4

Colony Formation Analysis of Human Gastric Cancer Derived Cell Line MK-45

MK-45 cells from a human gastric cancer derived cell line, were seeded in 6-well plates at 1000 cells/well. After the overnight culture, the cells were treated 10 μM of various CBDC compounds, 10 μg/ml CPT-11, or a combination of CBDC compounds and CPT-11 for three (3) hours. The CBDC compounds tested were: CBDC402, CBDC412, CBDC413, and CBDC418. The culture medium was changed and cells were cultured for 14 days, after which the colonies were fixed with methanol and stained with 0.1% crystal violet. A 3-hour treatment with 10 μM CBDC402 alone caused significant suppression of colony formation by MK-45 cells, while treatment with 10 μM CBDC412 caused a slight suppression of colony formation, and 10 μM CBDC413, or CBDC418 did not have an appreciable effect on colony formation. Treatment with 10 μg/ml CPT-11 caused significant suppression of colony formation, while addition of 10 μM CBDC402 appeared to augment the effect of 10 μg/ml CPT-11, resulting in almost complete suppression of colony formation. The combination of 10 μg/ml CPT-11 with 10 μM CBDC412 caused a slight suppression of colony formation above that seen with CPT-11 alone, while combinations of 10 μg/ml CPT-11 with 10 μM CBDC413, CBDC418.

Example 5

CBDC402 Specifically Abrogates the Cell Cycle G2 Checkpoint

Activated normal T cells and leukemic T cells (Jurkat cells) were treated with agents to induce accumulation of cells at G2 or M phase, and the effect of CBDC402 on progression of cells through cell cycle checkpoints was measured. After treatments, cells were harvested, DNA was stained, and the cell cycle stage for each cell was determined by flow cytometry as described above. In one experiment, activated normal T cells received no treatment (control), or were treated with bleomycin, CBDC402, or a combination of bleomycin and CBDC402. As shown in FIG. 10*a*, bleomycin treatment caused accumulation of a minor population of cells at G2 phase, and CBDC402 abolished the bleomycin-induced increase of activated normal T cells at G2 phase. In another experiment, leukemic T cells (Jurkat cells) received no treatment (control) or were treated with bleomycin, CBDC402, or a combination of bleomycin and CBDC402. As shown in FIG. 10*b*, bleomycin caused accumulation of a major population of cells at G2 phase, and CBDC402 abolished the large bleomycin-induced increase of leukemic T cells (Jurkat cells) at G2 phase. In another experiment, activated normal T cells received no treatment (control) or were treated with colchicine or a combination of CBDC420 and colchicine. As shown in FIG. 10*c*, colchicine caused an accumulation of cells in M phase, and CBDC402 did not affect the colchicine-induced increase of activated normal T cells at M phase. These results indicated the specificity of CBDC402 against G2 accumulation (and not M phase checkpoint), and indicated the specificity of CBDC402 against cancer cells.

Example 6

Synthesis of 4-bromo-benzoic acid 4-fluoro-phenyl ester

Ten ml of dioxane, 5 mmol (1.1 g) of 4-bromo-benzoic acid chlorine, and 5 mmol (0.56 g) of 4-fluoro-phenol were added to 50 ml four-mouth-flask sequentially and dissolved at room temperature. Triethylamine dissolved in dioxane was slowly dripped into this solution and the solution was stirred for three hours at room temperature. The precipitated crystals were filtered and extracted with benzene. The extracted solution was washed with sodium hydrocarbonate several times, magnesium anhydrate was added, and the resulting solution was dried and filtered. The solution was distilled under low pressure and crystallized. The row crystals were yellowish-white, weighing 1.37 g. A portion of this crystal (0.5 g) was dissolved in benzene and purified with 100 g of silica gel (Wako gel C-300, Japan). The purified product was white, and the purity was confirmed to 99.93% by liquid chromatography (LC). The structure was confirmed by NMR as follows. $^1$H NMR (400 MHz, DMSO-d6) δ 8.05 (2H, d, J=8.8 Hz), 7.83 (2H, d, J=8.8 Hz), 7.38-7.29 (4H, m) 13C NMR (100 MHz, DMSO-d6) δ 159.72 (C—F, d, J=240 Hz) 163.95 (C=O)

What is claimed is:

1. An in vitro method for suppressing or killing a DNA-damaged cell, comprising administering an effective amount of at least one compound that abrogates the cell cycle G2 checkpoint when administered to a cell, wherein the compound has the following structure:

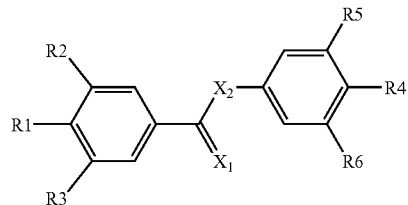

where either or both of benzene can be substituted with pyrazine, pyrimidine. piperazine, morpholine, cyclohexane, piperizine or pyridine; R1 is a halogen, bromine (Br), chlorine (Cl), fluorine (F), iodine (I). amino ($NH_2$), nitro ($NO_2$), hydroxy (OH),O-methyl ($OCH_3$), methyl ($CH_3$) or hydrogen (H); R2, R3, R4, R5 and R6 is bromine (Br), chlorine (Cl), fluorine (F), iodine (I), amino ($NH_2$), nitro ($NO_2$), methyl ($CH_3$), O-methyl ($OCH_3$), hydroxy (OH), $CH(CH_3)_2$, CHO, $CHOCH_3$, $O(CH_2)nCH_3$, $OCO(C_6H_{12})Cl$, $COOCH_3$ or hydrogen; X1 is nitrogen (NH), oxygen (O) or sulfate (S); and X2 is oxygen (O) or sulfate (S).

2. The method of claim 1, wherein the DNA-damaged cell has a DNA-damage-induced G2 checkpoint.

3. The method of claim 1, wherein the DNA-damaged cell has an impaired G1 checkpoint.

4. The method of claim 1, wherein the DNA-damaged cell is a cancer cell.

5. The method of claim 1, further comprising administering a DNA-damaging agent or a DNA-damaging treatment, wherein administering the compound increases the sensitivity of the cell to the DNA-damaging agent or DNA-damaging treatment.

6. A method of selectively targeting DNA-damaged cells according to the method of claim 1, comprising administering the compound to a population of cells comprising DNA-damaged cells and normal cells, wherein abrogation of the G2 checkpoint suppresses or kills DNA-damaged cells, and has little or no cytotoxic effect on normal cells.

7. The method of claim 6, further comprising administering a DNA-damaging agent or a DNA-damaging treatment.

8. The method of claim 6, wherein the DNA-damaged cells are cancer cells.

9. The method of claim 1, comprising administering at least one compound selected from: 4-chloro-benzoic acid 4-inethoxy-phenyl ester (CDBC004); 4-chloro-benzoic acid p-tolyl ester (CBDC401); 4-bromo-benzoic acid p-tolyl ester (CBDC402); 3,4,5-trifluoro-benzoic acid p-toly1 ester (CBDC403); 4-fluoro-benzoic acid 4-bromo-phenyl ester (CBDC404); 3,4-dichloro-benzoic acid p-tolyl ester (CBDC405); 4-tluoro-benzoic acid p-tolf ester (CBDC407); 4-chloro-benzoic acid 3,4-dimethyl-phenyl ester (CBDC409); 4-chloro-benzoic acid 4-hydroxy-phenyl ester (CBDC410); 4-fluoro-benzoic acid 4-hydroxy-phenyl ester (CBDC411); 4-bromo-benzoic acid 4-fluoro-phenyl ester (CBDC412); 4-brosno-benzoic acid 4-trifluoromethyl-phenyl ester (CBDC413); 4-bromo-benzoic acid 4-hydroxy-phenyl ester (CBDC414); 4-bromo-benzoic acid 4-trifluoromethoxy-phenyl ester (CBDC415); 4-Bromo-benzoic acid 6-methyl-pyridin-3-yl ester (CBDC418); 4-bromo-thiobenzoic acid 0-p-tolyl ester (CBDC440); 4-bromo-dithiobenzoic acid p-tolyl ester (CBDC441); and 4-bromo-thiobenzoic acid S-p-tolyl ester (CBDC442).

10. The method of claim 1, comprising administering 4-chloro-benzoic acid 4-methoxy-phenyl ester (CBDC004) having the structure:

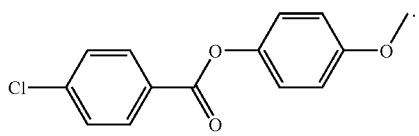

11. The method of claim 1, comprising administering 4-chloro-benzoic acid p-tolyl ester (CBDC401) having the structure:

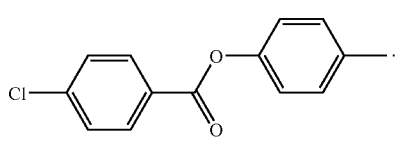

12. The method of claim 1, comprising administering 4-bromo-benzoic acid p-tolyl ester (CBDC402) having the structure:

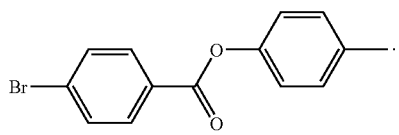

13. The method of claim 1, comprising administering 3,4,5-trifluoro-benzoic acid p-tolyl ester (CBDC403) having the structure:

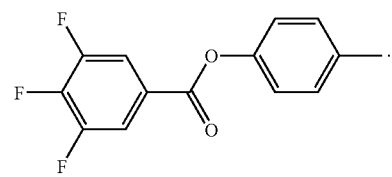

14. The method of claim 1, comprising administering 4-fluoro-benzoic acid 4-bromo-phenyl ester (CBDC404) having the structure:

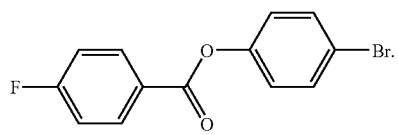

15. The method of claim 1, comprising administering 3,4-dichioro-benzoic acid p-tolyl ester (CBDC405) having the structure:

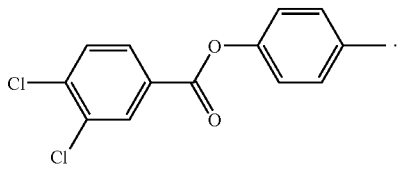

16. The method of claim 1, comprising administering 4-fluoro-benzoic acid p-tolyl ester (CBDC407) having the structure:

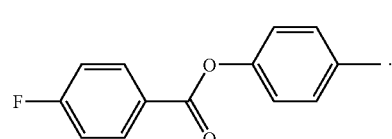

17. The method of claim 1, comprising administering 4-chloro-benzoic acid 3,4-dimethyl-phenyl ester (CBDC409) having the structure:

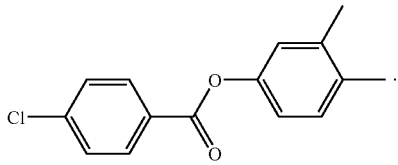

18. The method of claim 1, comprising administering 4-chloro-benzoic acid 4-hydroxy-phenyl ester (CBDC410) having the structure:

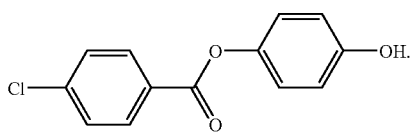

19. The method of claim 1, comprising administering 4fluoro-benzoic acid 4-hydroxy-phenyl ester (CBDC411) having the structure:

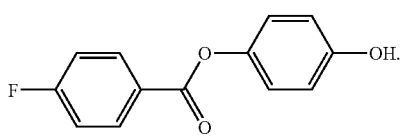

20. The method of claim 1, comprising administering 4-bromo-benzoic acid 4-fluoro-phenyl ester (CBDC412) having the structure:

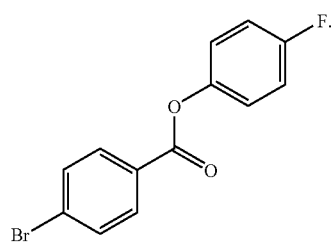

21. The method of claim 1, comprising administering 4-bromo-benzoic acid 4-trifluoromethyl-phenyl ester (CBDC413) having the structure:

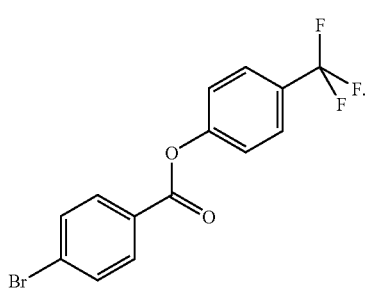

22. The method of claim 1, comprising administering 4-bromo-benzoic acid 4-hydroxy--phenyl ester (CBDC414) having the structure:

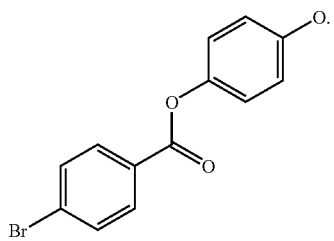

23. The method of claim 1, comprising administering 4-bromo-benzoic acid 4-trifluoromethoxy-phenyl ester (CBDC415) having the structure:

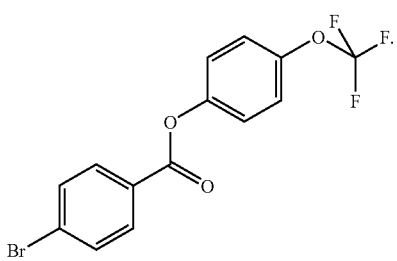

24. The method of claim 1, comprising administering 4-bromo-benzoic acid 6-methyl-pyridin--3-yl ester (CBDC418) having the structure:

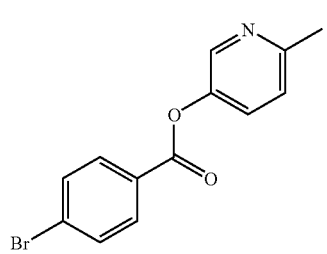

25. The method of claim 1, comprising administering 4-bromo-thiobenzoic acid 0-p-tolyl ester (CBDC440) having the structure:

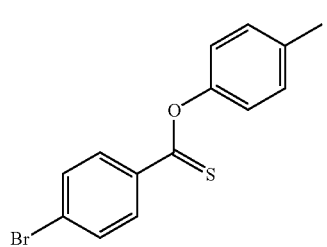

26. The method of claim 1, comprising administering 4-bromo-dithiobenzoic acid p-tolyl ester (CBDC441) having the structure:

27. The method of claim 1, comprising administering 4-bromo-thiobenzoic acid S-p-tolyl ester (CBDC442) having the structure:
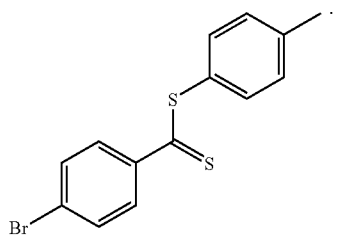
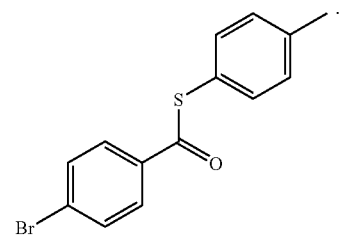
* * * * *